United States Patent [19]

Hartman et al.

[11] Patent Number: 5,397,791

[45] Date of Patent: Mar. 14, 1995

[54] FIBRINOGEN RECEPTOR ANTAGONISTS

[75] Inventors: George D. Hartman, Lansdale; John D. Prugh, Chalfont; Wasyl Halczenko, Lansdale; Melissa Egbertson, Ambler; Nathan Ihle, Perkasie, all of Pa.

[73] Assignee: Merck & Co., Inc., Rahway, N.J.

[21] Appl. No.: 103,846

[22] Filed: Aug. 9, 1993

[51] Int. Cl.$^6$ ............... A61K 31/445; C07D 401/10; C07D 409/06; C07D 411/06

[52] U.S. Cl. .................. 514/318; 514/183; 514/210; 514/233.8; 514/235.2; 514/255; 514/256; 514/314; 514/321; 514/323; 514/331; 514/338; 540/200; 540/480; 544/111; 544/133; 544/145; 544/148; 544/335; 544/368; 546/167; 546/193; 546/197; 546/201; 546/235; 546/270; 548/307.1; 548/311.7; 548/204; 549/32

[58] Field of Search ........... 546/167, 193, 197, 235, 546/201, 270, 111; 544/133, 145, 335, 148, 368; 540/200, 480; 548/307.1, 311.7, 204; 349/32; 514/183, 210, 233.8, 235.2, 255, 256, 314, 318, 321, 323, 331, 338

[56] References Cited

U.S. PATENT DOCUMENTS

| | | | |
|---|---|---|---|
| 4,064,255 | 12/1977 | Champseix et al. | 424/267 |
| 4,122,255 | 10/1978 | Krapcho | 542/421 |
| 4,243,807 | 1/1981 | Friebe et al. | 546/232 |
| 4,313,947 | 2/1982 | Nakagawa et al. | 514/312 |
| 4,622,331 | 11/1986 | Jozic | 514/331 |
| 5,030,654 | 7/1991 | Barnish et al. | 514/510 |
| 5,037,808 | 8/1991 | Tjoeng | 514/20 |
| 5,064,814 | 11/1991 | Klein et al. | 514/18 |

FOREIGN PATENT DOCUMENTS

| | | |
|---|---|---|
| 0229391A1 | 7/1987 | European Pat. Off. . |
| 0352249A1 | 1/1990 | European Pat. Off. . |
| 0372486A2 | 6/1990 | European Pat. Off. . |
| 0381033A1 | 8/1990 | European Pat. Off. . |
| 0384362A2 | 8/1990 | European Pat. Off. . |
| 0405537A | 2/1991 | European Pat. Off. . |
| 0478328A1 | 1/1992 | European Pat. Off. . |
| 0478362A2 | 1/1992 | European Pat. Off. . |
| 0478363A2 | 1/1992 | European Pat. Off. . |
| 0479481A2 | 8/1992 | European Pat. Off. . |

OTHER PUBLICATIONS

Zubay, G. "Biochemistry" Addison–Wesley Publishing pp. 867–870 (1986).
Stryer, L. "Biochemistry" W. H. Freeman & Co. Publishing pp. 16–21 (1988).
Hartman et al "Non–peptide Fibrinogen Receptor Antagonist" J. Med. Chem. 35 pp. 4640–4642 (1992).

*Primary Examiner*—Celia Chang
*Attorney, Agent, or Firm*—Richard S. Parr; Melvin Winokur; Paul D. Matukaitis

[57] ABSTRACT

Fibrinogen receptor antagonists having the formula

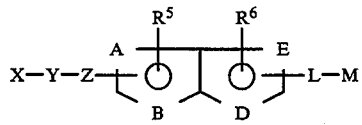

for example

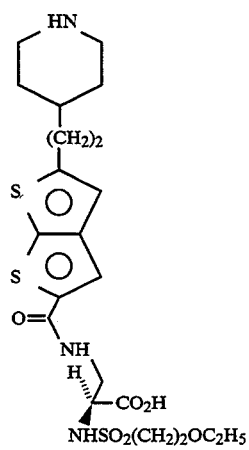

8 Claims, No Drawings

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in Science, 238,491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide sequence arginine-glycine-aspartic acid (RGD) as a glycoprotein IIb/IIIa recognition site. These arginine-glycine-aspartic acid containing proteins are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in Proc. Nat'l Acad. Sci. U.S.A., 84; 6471–6475, (1987), describes an Arg-Gly-Asp directed adhesion receptor expressed by human endothethial cells that is structurally similar to the IIb/IIIa complex on platelets but is antigentically and functionally distinct. This receptor is directly involved in endothelial cell attachment to fibrinogen, von Willebrand factor, and vitronectin.

Pierschbacher and Rouslahti, in J. of Biol. Chem., 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between nonterminal residues Pen and Cys, rendered the peptide much less effective at inhibiting attachment to fibronectin.

In Proc. Nat'l Acad. Sci. U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079. Ruggeri et al., Proc. Nat'l Acad. Sci. U.S.A., 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., Biochem. 23, 1767–1774 (1984); Ginsberg et al., J. Biol. Chem. 260(7), 3931–3936 (1985); and Hayerstick et al., Blood 66(4), 946– 952 (1985). Other inhibitors are disclosed in Eur. Pat. App. Nos. 275,748 and 298,820.

A number of low molecular weight polypeptide factors have been isolated from snake venom. These factors apparently have high affinity for the gpIIb/IIIa complex. For example, Huang et al., J. Biol Chem., 262, 16157–16163 (1987); Huang et al., Biochemistry 28, 661–666 (1989) describe the primary structure of the venom trigramin which is a 72 amino acid polypeptide that contains the RGD subunit. Echistatin is another venom which has high affinity for the gpIIb/IIIa complex. This polypeptide contains 49 amino acids and has the RGD subunit and various disulfide bridges. Gan et al., J. Biol. Chem., 263, 19827–19832 (1988). See also, Dennis et al., Proc. Nat'l Acad. Sci. USA, 87, 2471 $\propto$ 2475 (1989). However, these snake venom factors also have high affinity for other members of the adhesive protein receptor family including the vitronectin and fibronectin receptors so are not selective for the gpIIb/IIIa complex.

While it is known that the tripeptide sequence Arg-Gly-Asp is present in Certain polypeptides that can duplicate or inhibit the cell attachment-promoting effects of fibronectin and vitronectin, the tri-peptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gpIIb/IIIa receptor. U.S. Pat. No. 5,037,808 discloses guanidino peptide mimetic compounds that retain an Asp residue which inhibit platelet aggregation. The application PCT/US90/02746 describes the use of antibody-polypeptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the $R^1$—A—(W—$)_a$—X—$(CH_2)_b$—$(Y)_c$—B—Z—COOR wherein $R^1$ is a guandidino or amidino moiety and A and B are chosen from specific monosubstituted aryl or heterocyclic moieties.

The present invention provides novel fibrinogen receptor antagonists that have significant platelet aggregation inhibitory activity which is useful for prevention of blood clot formation. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a fibrinogen receptor antagonist of the formula:

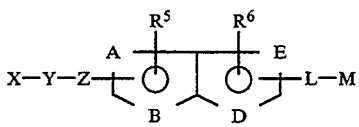

for example

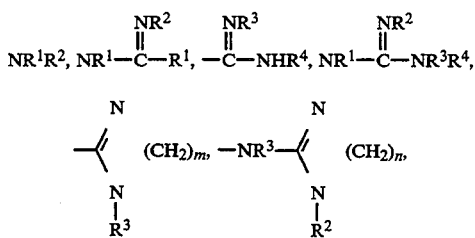

DETAILED DESCRIPTION OF THE INVENTION

This invention pertains to compounds of the general formula I

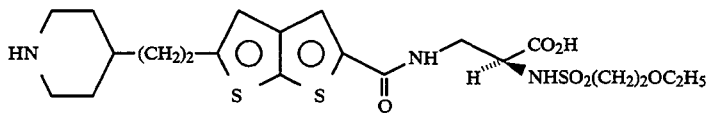

and the pharmaceutically acceptable salts thereof wherein: A, B, D and E are independently selected from C, N, O and S and wherein:
X is

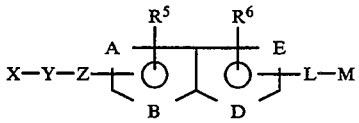

or a 4- to 10- membered mono- or polycyclic aromatic or nonaromatic ring system containing 0, 1, 2, 3 or 4 heteroatoms selected from N,O and S and either unsubstituted or substituted with $R^1$, $R^2$, $R^3$ or $R^4$, wherein $R^1$, $R^2$, $R^3$ and $R^4$ are independently selected from the group consisting of hydrogen, $C_{1-10}$ alkyl, aryl $C_{0-8}$ alkyl, OXO, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy, or hydroxy $C_{0-6}$ alkyl, where m and n are integers independently chosen from 2-5;

Y is $C_{0-8}$ alkyl, $C_{0-8}$ alkyl ($C_{4-10}$ cycloalkyl), $C_{0-8}$ alkyl-$NR^3$—CO—$C_{0-8}$ alkyl, $C_{0-8}$ alkyl-CONR$^3$—$C_{0-8}$ alkyl, $C_{0-8}$ alkyl-O—$C_{0-8}$ alkyl, $C_{0-8}$ alkyl-S(O$_n$)—$C_{0-8}$ alkyl, or $C_{0-8}$ alkyl-SO$_2$—NR$^3$—$C_{0-8}$ alkyl-, $C_{0-8}$ alkyl-NR$^3$—SO$_2$—$C_{0-8}$ alkyl-, $C_{0-8}$ alkyl-CO—$C_{0-8}$ alkyl, $(CH_2)_{0-6}$ aryl$(CH_2)_{0-6}$,

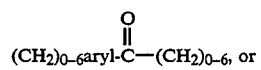

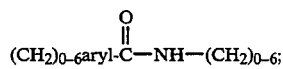

Z and L are independently chosen from

$(CH_2)_mS(CH_2)_n$, $(CH_2)_mSO(CH_2)_n$, $(CH_2)_mSO_2NR^3(CH_2)_n$, $(CH_2)_mNR^3SO_2(CH_2)_n$, $(CH_2)_mCR^3$=$CR^4(CH_2)_n$, $(CH_2)_mC$≡$C(CH_2)_n$, $(CH_2)_m$, and $(CH_2)_mO(CH_2)_n$, where m and n are integers independently chosen from 0-6;

$R^5$ and $R^6$ are independently chosen from: hydrogen, $C_{1-46}$ alkyl, $C_{0-6}$ alkylcarboxy $C_{0-6}$ alkyl, $C_{0-6}$ alkyloxy $C_{0-6}$ alkyl, hydroxy $C_{0-6}$ alkyl, aryl $C_{0-6}$ alkyl, and halogen;

M is:

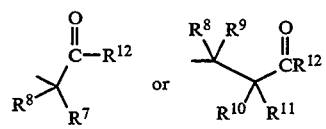

wherein $R^7$, $R^8$, $R^9$, $R^{10}$, $R^{11}$ are independently chosen from: hydrogen, fluorine, $C_{1-8}$ alkyl, hydroxyl, hydroxy $C_{1-6}$ alkyl, carboxy $C_{0-6}$ alkyl, $C_{1-6}$ alkyloxy, aryl $C_{0-6}$ alkyloxy, $C_{1-6}$ alkylcarbonyl, aryl $C_{0-6}$ alkylcarbonyl, $C_{1-6}$ alkylcarbonyloxy, aryl $C_{0-6}$ alkylcarbonyloxy, $C_{1-6}$ alkylaminocarbonyloxy $C_{0-6}$ alkyl, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$-alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $_{0-6}$ alkylcarbonyl $C_{0-6}$ alkyl, $C_{1-6}$ alkylthiocarbonylamino $C_{0-6}$ alkyl, and aryl $C_{0-6}$ alkylthiocarbonylamino $C_{0-6}$ alkyl, and wherein groups may be unsubstituted or substituted with one or more substituents selected from $R^1$ and $R^2$; and $R^{12}$ is chosen from hydroxy, $C_{1-8}$ alkyloxy, aryl $C_{0-6}$ alkyloxy, $C_{1-8}$ alkylcarbonyloxy $C_{1-4}$ alkyloxy, and aryl $C_{0-8}$ alkylcarbonyloxy $C_{1-4}$ alkyloxy, or a naturally occurring L- or D-amino acid joined by an amide linkage and wherein the carboxylic acid moiety of said amino acid is as the free acid or is esterified by $C_{1-6}$ alkyl.

When substituent $R^1$, $R^2$, $R^3$, $R^4$, $R^5$, $R^6$, $R^7$, $R^8$, $R^9$, $R^{10}$, $R^{11}$, $R^{12}$, X, Y, Z, L or M includes the definition $C_0$, (e.g. aryl $C_0$ alkyl), the group modified by $C_0$ is not present in the substituent.

"Aryl" means a mono- or polycyclic system composed of 5- and 6-membered aromatic rings containing 0, 1, 2, 3, or 4 heteroatoms chosen from N, O or S and either unsubstituted or substituted with $R^1$.

"Alkyl" means straight or branched chain alkane, alkene or alkyne.

"Halogen" includes fluorine, chlorine, iodine and bromine.

"OXO" means=O.

"Thio" means=S.

A preferred embodiment of the present invention are compounds of the general formula, and the pharmaceutically acceptable salts, wherein

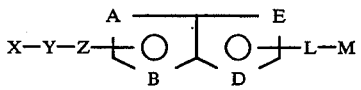

A, B, D and E are independently chosen from C, N, O and S;

X is —$NR^1R^2$,

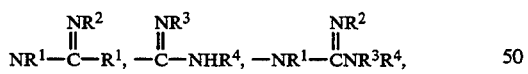

or a 4- to 10-membered mono- or polycyclic aromatic or nonaromatic ring system containing 0, 1, 2, 3 or 4 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen, $C_{1-10}$ alkyl, or aryl $C_{0-8}$ alkyl;

Y is $C_{0-8}$ alkyl, $C_{0-8}$ alkyl-$NR^3$—CO—$C_{0-8}$ alkyl, $C_{0-8}$ alkyl-$CONR^3$—$C_{0-8}$ alkyl, $C_{0-8}$ alkyl-O—$C_{0-8}$ alkyl, $C_{0-8}$ alkyl-S($O_n$)—$C_{0-8}$ alkyl, or $C_{0-8}$ alkyl-$SO_2$—$NR^3$—$C_{0-8}$ alkyl-;

Z and L are independently chosen from:

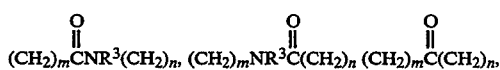

$(CH_2)_mSO_2(CH_2)_n$, $(CH_2)_mSO_2NR^3(CH)_n$, $(CH)_mNR^3SO_2(CH_2)_n$, and $(CH_2)_m$ where m and n are integers independently chosen from 0–6;

M is:

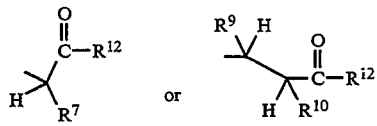

wherein $R^7$, $R^9$, and $R^{10}$ are independently chosen from: hydrogen, fluorine, hydroxyl, $C_{1-8}$ alkyl, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$-alkyl, aryl $C_{0-8}$ alkyloxycarbonylamino $C_{0-8}$ alkyl, $C_{1-8}$ alkylcarbonylamino $C_{0-6}$ alkyl, aryl $_{0-6}$ alkylcarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, aryl $C_{0-8}$ alkylaminocarbonylamino $C_{0-6}$ alkyl, $C_{0-8}$ alkylaminocarbonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, and aryl $C_{0-6}$ alkylcarbonyl $C_{0-6}$ alkyl;

$R^{12}$ is chosen from hydroxy, $C_{1-8}$ alkyloxy, aryl $C_{0-6}$ alkyloxy, $C_{1-8}$ alkylcarbonyloxy $C_{1-4}$ alkyloxy, and aryl $C_{0-8}$ alkylcarbonyloxy $C_{1-4}$ alkyloxy.

A more preferred embodiment of the present invention encompasses compounds of the general formula

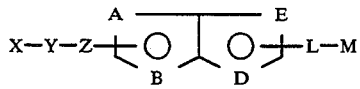

and the pharmaceutically acceptable salts, wherein: A, B, D and E are independently chosen from C, N,O and S, wherein X is —$NR^1R^2$,

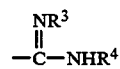

or a 4- to 8-membered nonaromatic ring system containing 0, 1, 2, 3 or 4 heteroatoms selected from N and O wherein $R^1$, $R^2$, $R^3$ and $R^4$ are independently selected from the group consisting of hydrogen, $C_{1-10}$ alkyl, or aryl $C_{0-8}$ alkyl;

Y is $C_{0-8}$ alkyl, $C_{0-8}$ alkyl-$NR^3$—CO—$C_{0-8}$ alkyl, $C_{0-8}$ alkyl-$CONR^3$—$C_{0-8}$ alkyl, $C_{0-8}$ alkyl-O—$C_{0-8}$ alkyl, or $C_{0-8}$ alkyl-S($O_n$)—$C_{0-8}$ alkyl;

Z and L are independently chosen from:

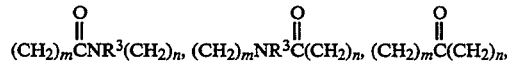

$(CH_2)_mSO_2(CH_2)_n$, and $(CH_2)_m$, where m and n are integers independently chosen from 0–6;

M is:

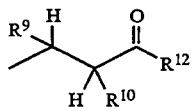

wherein $R^9$ and $R^{10}$ are independently chosen from: hydrogen, fluorine, $C_{1-8}$ alkyl, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$-alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-8}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, or aryl $C_{0-6}$ alkylcarbonyl $C_{0-6}$ alkyl; and $R^{12}$ is chosen from hydroxy, $C_{1-8}$ alkyloxy, and aryl $C_{0-6}$ alkyloxy.

In another preferred embodiment, compounds of the invention have the general formula I

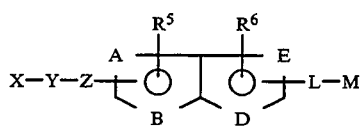

and the pharmaceutically acceptable salts thereof wherein: A, B, D and E are independently selected from C, N, O and S and wherein:

X is

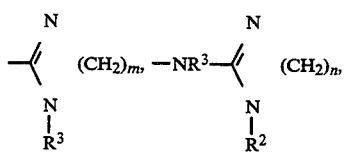

or a 4- to 10-membered mono- or polycyclic aromatic or nonaromatic ring system containing 0, 1, 2, 3 or 4 heteroatoms selected from N, O and S and either unsubstituted or substituted with R2 or R3, wherein R2 and R3 are independently selected from the group consisting of hydrogen, $C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy, or hydroxy $C_{0-6}$ alkyl, where m and n are integers independently chosen from 2-5;

Y is $C_{0-8}$ alkyl, $C_{0-8}$ alkyl ($C_{4-10}$ cycloalkyl), $C_{0-8}$ alkyl-$NR^3$—CO—$C_{0-8}$ alkyl, $C_{0-8}$ alkyl-$CONR^3$—$C_{0-8}$ alkyl, $C_{0-8}$ alkyl-O—$C_{0-8}$ alkyl, $C_{0-8}$ alkyl-$S(O_n)$—$C_{0-8}$ alkyl, or $C_{0-8}$ alkyl-$SO_2$—$NR^3$—$C_{0-8}$ alkyl-, $C_{0-8}$ alkyl-$NR^3$—$SO_2$—$C_{0-8}$ alkyl-, $C_{0-8}$ alkyl-CO—$C_{0-8}$ alkyl, $(CH_2)_{0-6}$ aryl$(CH_2)_{0-6}$,

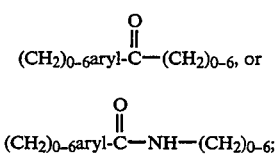

Z and L are independently chosen from

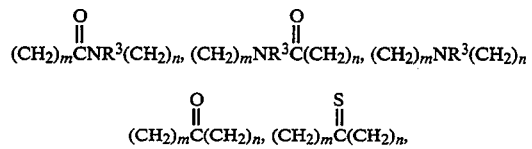

$(CH_2)_m SO_2(CH_2)_n$, $(CH_2)_m S(CH_2)_n$, $(CH_2)_m SO(CH_2)_n$, $(CH_2)_m SO_2 NR^3(CH_2)_n$, $(CH_2)_m NR^3 SO_2(CH_2)_n$, $(CH_2)_m CR^3=CR^2CH_2)_n$, $(CH_2)_m C\equiv C(CH_2)_n$, $(CH_2)_m$, and $(CH_2)_m O(CH_2)_n$, where m and n are integers independently chosen from 0–6;

$R^5$ and $R^6$ are independently chosen from: hydrogen, $C_{1-6}$ alkyl, $C_{0-6}$ alkylcarboxy $C_{0-6}$ alkyl, $C_{0-6}$ alkyloxy $C_{0-6}$ alkyl, hydroxy $C_{0-6}$ alkyl, aryl $C_{0-6}$ alkyl, and halogen;

M is:

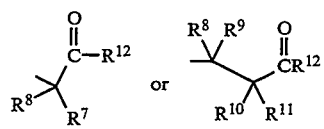

wherein $R^7$, $R^8$, $R^9$, $R^{10}$, $R^{11}$ are independently chosen from: hydrogen, fluorine, $C_{1-8}$ alkyl, hydroxyl, hydroxy $C_{1-6}$ alkyl, carboxy $C_{0-6}$ alkyl, $C_{1-6}$ alkyloxy, aryl $C_{0-6}$ alkyloxy, $C_{1-6}$ alkylcarbonyl, aryl $C_{0-6}$ alkylcarbonyl, $C_{1-6}$ alkylcarbonyloxy, aryl $C_{0-6}$ alkylcarbonyloxy, $C_{1-6}$ alkylaminocarbonyloxy, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$-alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $_{0-6}$ alkylcarbonyl $C_{0-6}$ alkyl, $C_{1-6}$ alkylthiocarbonylamino $C_{0-6}$ alkyl, and aryl $C_{0-6}$ alkylthiocarbonylamino $C_{0-6}$ alkyl, and wherein groups may be unsubstituted or substituted with one or more substituents selected from $R^2$ and $R^3$;

$R^{12}$ is chosen from hydroxy, $C_{1-8}$ alkyloxy, aryl $C_{0-6}$ alkyloxy, $C_{1-8}$ alkylcarbonyloxy $C_{1-4}$ alkyloxy, and aryl $C_{0-8}$ alkylcarbonyloxy $C_{1-4}$ alkyloxy, or a naturally occurring L- or D-amino acid joined by an amide linkage and wherein the carboxylic acid moiety of said amino acid is as the free acid or is esterified by $C_{1-6}$ alkyl.

More preferably, these compounds, and their pharmaceutically acceptable salts, have the formula

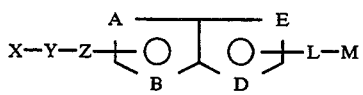

wherein A, B, D and E are independently chosen from C, N, O and S;

X is a 4- to 10-membered mono- or polycyclic aromatic or nonaromatic ting system containing 0, 1, 2, 3 or 4 heteroatoms selected from N, O and S and either unsubstituted or substituted with hydrogen, $C_{1-10}$ alkyl, or aryl $C_{0-8}$ alkyl;

Y is $C_{0-8}$ alkyl, $C_{0-8}$ alkyl-$NR^3$—CO—$C_{0-8}$ alkyl, $C_{0-8}$ alkyl-$CONR^3$—$C_{0-8}$ alkyl, $C_{0-8}$ alkyl-O—$C_{0-8}$ alkyl, $C_{0-8}$ alkyl-$S(O_n)$—$C_{0-8}$ alkyl, or $C_{0-8}$ alkyl-$SO_2$—$NR^3$—$C_{0-8}$ alkyl-;

$R^3$ is selected from hydrogen, $C_{1-10}$ alkyl, or aryl $C_{0-8}$ alkyl;

Z and L are independently chosen from:

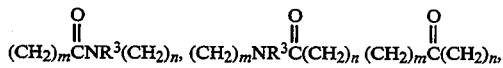

$(CH_2)_mSO_2(CH_2)_n$, $(CH_2)_mSO_2NR^3(CH)_n$, $(CH)_mNR^3SO_2(CH_2)_n$, and $(CH_2)_m$ where m and n are integers independently chosen from 0–6;

M is:

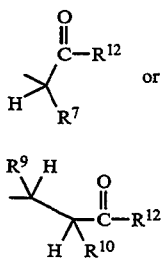

wherein $R^7$, $R^9$, and $R^{10}$ are independently chosen from: hydrogen, fluorine, hydroxyl $C_{1-8}$ alkyl, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$-alkyl, aryl $C_{0-8}$ alkyloxycarbonylamino $C_{0-8}$ alkyl, $C_{1-8}$ alkylcarbonylamino $C_{0-6}$ alkyl, aryl $_{0-6}$ alkylcarbonylamino $C_{0-6}$ alkyl, $C_{0-8}$ alkylaminosulfonylamino $C_{0-6}$ alkyl, aryl $C_{0-8}$ alkylaminocarbonylamino $C_{0-6}$ alkyl, $C_{0-8}$ alkylaminocarbonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, and aryl $C_{0-6}$ alkylcarbonyl $C_{0-6}$ alkyl;

$R^{12}$ is chosen from hydroxy, $C_{1-8}$ alkyloxy, aryl $C_{0-6}$ alkyloxy, $C_{1-8}$ alkylcarbonyloxy $C_{1-4}$ alkyloxy, and aryl $C_{0-8}$ alkylcarbonyloxy $C_{1-4}$ alkyloxy.

Even more preferably, these compounds, and their pharmaceutically acceptable salts, have the formula

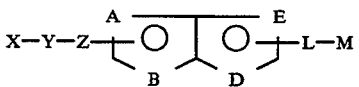

wherein: A, B, D and E are independently chosen from C, N, O and S, wherein

X is a 4- to 8-membered nonaromatic ting system containing 0, 1, 2, 3 or 4 heteroatoms selected from N and O;

Y is $C_{0-8}$ alkyl, $C_{0-8}$ alkyl-$NR^3$—CO—$C_{0-8}$ alkyl, $C_{0-8}$ alkyl-$CONR^3$—$C_{0-8}$ alkyl, $C_{0-8}$ alkyl-O—$C_{0-8}$ alkyl, or $C_{0-8}$ alkyl-$S(O_n)$—$C_{0-8}$ alkyl;

$R^3$ is hydrogen, $C_{l-10}$ alkyl, or aryl $C_{0-8}$ alkyl;

Z and L are independently chosen from:

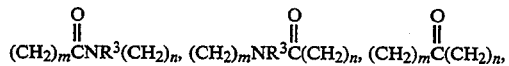

where m and n are integers independently chosen from 0–6;

M is:

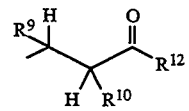

wherein $R^9$ and $R^{10}$ are independently chosen from: hydrogen, fluorine, $C_{1-8}$ alkyl, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$-alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-8}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, or aryl $C_{0-6}$ alkylcarbonyl $C_{0-6}$ alkyl, and $R^{12}$ is chosen from hydroxy, $C_{1-8}$ alkyloxy, and aryl $C_{0-6}$ alkyloxy.

Naturally occurring L- or D-amino acids include, for example, those naturally occurring L-amino acids present in humans, e.g. protein amino acids,, including L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine, and those naturally occurring D-amino acids which are non-protein amino acids, such as those found, for example, in antibiotic substances produced by bacteria and fungi, including D-valine, D-asparagine, D-glutamate, D-ornithine, D-phenylalanine, D-leucine, D-cysteine, and D-aspartate. (see Zubay "BIOCHEMISTRY" Addison-Wesley Publishing Company, Inc. (Reading, MA) 1983 pp. 867–870 and Stryer "BIOCHEMISTRY" W. H. Freeman and Company (New York, N.Y.) 3rd Edition 1988 pp. 16–21.

The following examples illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

SCHEME 1
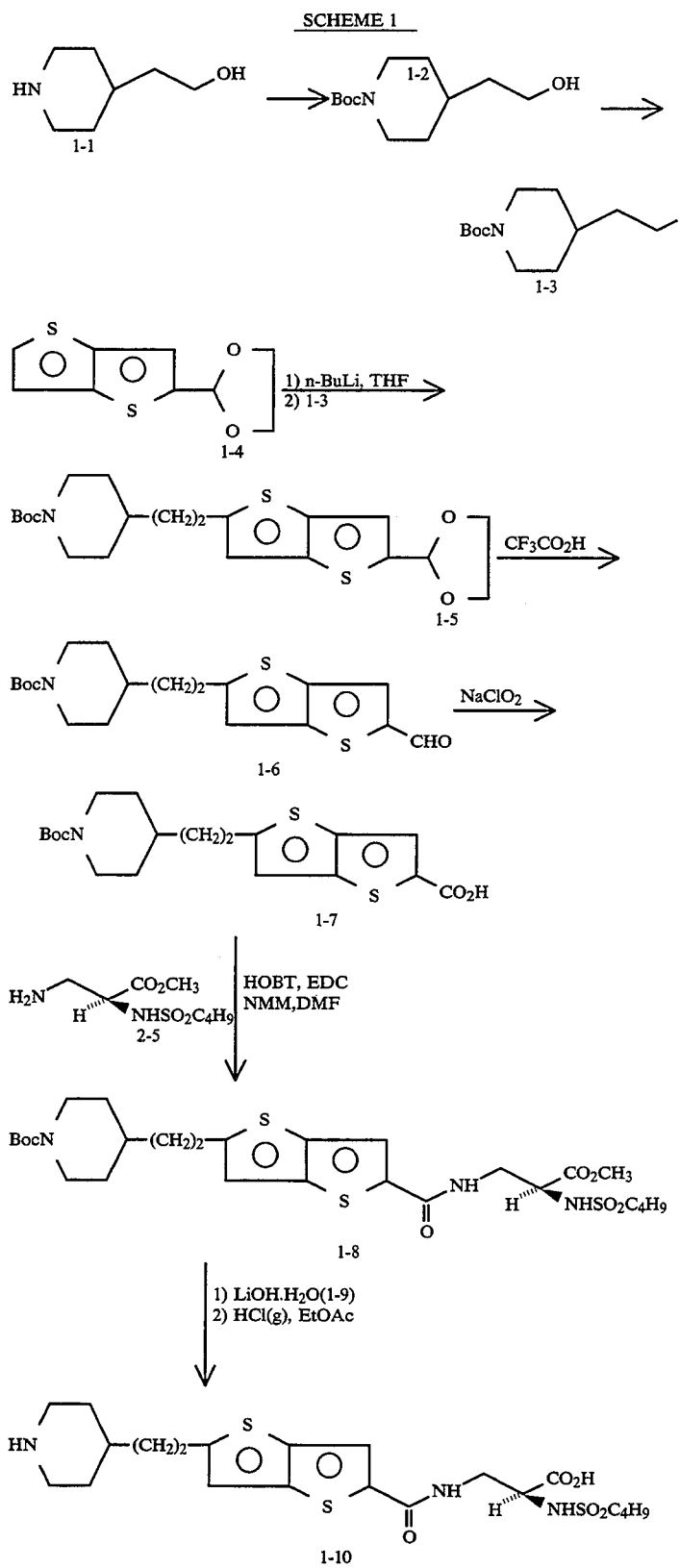
2(N-t-Butyloxycarbonylpiperidin-4-yl)ethanol (1-2)
To a stirred solution of 4-piperidineethanol 8(Aldrich) (18.7 g, 0.14 mol) and DMF (200 mL) at 0° C. was added N-tert-butoxycarbonyl anhydride (31 g, 0.14 mol). After 1 hr the cooling bath was removed and the reaction mixture stirred for 20 hr. The reaction mixture was diluted with ether and then washed with water (2×) and brine, dried (MgSO$_4$), and concentrated to furnish 1-2 as a colorless oil.

TLC R$_f$=0.25 (40% ethyl acetate/hexanes); $^1$H NMR (300 MHz, CDCl$_3$) δ4.09 (bs, 2H),3.72 (t, J=7 Hz, 2H), 2.70 (m, 2H), 1.75–1.10 (m, 7H), 1.46 (s, 9H).

2-(N-t-Butyloxycarbonylpiperidin-4-yl)ethyl iodide (1-3)

To a stirring solution of 1-2 (18.0 g, 77 mmol), triphenylphosphine (22.2 g, 85 mmol), imidazole (7.9 g, 115 mmol), and benzene (800 mL) at ambient temperature was added iodine (22.0 g, 85 mmol). After 5 min the heterogeneous reaction mixture was filtered and the filtrate concentrated. Flash chromatography (silica gel, 10% ethyl acetate/hexanes) gave 1-3 as an oil. TLC R$_f$=0.95 (50% ethyl acetate/hexanes);

$^1$H NMR (300 MHz, CDCl$_3$) δ4.11 (m, 2H), 3.24 (t, J=6 Hz, 2H), 2.72 (m, 2H), 1.82 (dt, J=7, 7 Hz, 2H), 1.75–1.55 (m, 5H), 1.48 (s, 9H), 1.12 (m, 2H).

5-[2-(N-t-Butyloxycarbonylpiperidin-4-yl)ethyl]-thieno[3,2-b]thiophene-2-carboxaldehyde ethylene glycol acetal (1-5)

A solution of thieno[3,2-b]thiophene-2-carboxaldehyde ethylene glycol acetal (1-4) (J. D. Prugh, et al. J. Med. Chem. 1991, 34, 1805–1818) (0.212 g, 1.0 mmol) in THF (10 ml) cooled to −78° was treated with n-BuLi(1.1 mmol in hexane) with stirring for 2 hrs. Then, a solution of 1-3 (0.339 g) in 2 ml THF was added and the resulting solution was allowed to slowly warm to room temperature over 16 hrs. The solvent was removed and the residue quenched with Ether/H$_2$O and the organic phase was separated, dried (MgSO$_4$) and concentrated. The residue was purified by flash chromatography on silica gel eluting with 10–20% EtOAc/hexane to give pure 1-5.

$^1$H NMR (300 MHz, CDCl$_3$) δ1.14 (2H, m), 1.46 (9H, s), 1.70 (5H, m), 2.65 (2H, t), 2.90 (2H, t), 4.08 (8H, m), 6.14 (1H, s), 6.91 (1H, s), 7.26 (1H, s).

5-[2-(N-t-Butyloxycarbonylpiperidin-4-yl)ethyl]-thieno[3,2-b]thiophene-2-carboxaldehyde (1-6)

A solution of 1-5 (0.458 g, 1.08 mmol) in acetone (20 ml) was treated with 2.2 g of trifluoroacetic acid for 5 minutes, then promptly diluted with EtOAc (100 ml). This was extracted with saturated Na$_2$CO$_3$ solution (25 ml), H$_2$O, dried (MgSO$_4$) and concentrated to give 1-6.

$^1$H NMR (300 MHz, CDCl$_3$) δ1.15 (2H, m), 1.45 (9H, s), 1.71 (4H, m), 2.69 (2H, t), 2.96 (2H, t), 4.10 (4H, m), 7.03 (1H, s), 7.86 (1H, s), 9.93 (1H, s).

5-[2-(N-t-Butyloxycarbonylpiperidin-4-yl)ethyl]-thieno[3,2-b]thiophene-2-carboxylic acid (1-7)

A solution of 1-6 (0.046 g, 0.1 mmol) in t-butanol (3 ml) at room temperature was treated with a solution of NaClO$_2$ (0.1 g, 1.1 mmol) and NaH$_2$PO$_4$. H$_2$O (0.10 g, 0.72 mmol) in 1 ml H$_2$O and 1 ml of 2-methyl-2-butene with stirring at room temperature for 16 hrs. The reaction mixture was concentrated and partitioned between EtOAc (10 ml) and 3 ml of 1N NaHSO$_4$. The organic phase was dried (MgSO$_4$), concentrated and the solvent was removed. The residue was triturated with hexane to give pure 1-7.

$^1$H NMR (300 MHz, CDCl$_3$) δ1.18 (2H, m), 1.46 (9H, s), 1.70 (3H, m), 2.69 (2H, t), 2.93 (2H, t), 4.10 (2H, bd), 7.00 (1H, s), 7.99 (1H, s).

5-[2-(N-t-Butyloxycarbonylpiperidin-4-yl)ethyl]-thieno[3,2-b]-thiophene-2-N-[3-(methyl 2(S)-n-butylsulfonylamino)propionate]-carboxamide (1-8,)

A solution of 1-7 (0.2 g, 0.5 mmol), methyl 2(S)-n-butylsulfonylamino-3-aminopropionate (2-5) (synthesis is described in Scheme 2) (0.14 g, 0.5 mmol), HOBT (0.07 g, 0.55 mmol), EDC (0.11 g, 0.58 mmol) in DMF (10 ml) was treated at room temperature with N-methylmorpholine (NMM) (0.15 g, 1.5 mmol) and the resulting solution was stirred for 18 hrs. The reaction mixture was poured into H$_2$O (200 ml) and extracted with EtOAc. The organic extract was washed with 1N KHSO$_4$ solution, saturated NaHCO$_3$ solution, brine, and then dried (MgSO$_4$). The solvent was removed and the residue purified by flash chromatography on silica gel eluting with 55% EtOAc/hexane to give pure 1-8.

$^1$H NMR (300 MHz, CDCl$_3$) δ0.90 (3H, t), 1.15 (2H, m), 1.27 (2H, m), 1.46 (9H, s), 1.72 (5H, m), 2.78 (2H, t), 2.91 (2H, t), 3.05 (2H, t), 4.10 (2H, m), 4.39 (1H, bs), 6.00 (1H, bd), 6.92 (1H, s), 7.18 (1H, m), 7.72 (1H, s).

5-[2-(Piperidin-4-yl)ethyl]thieno[3,2-b]thiophene-2-N-[3-(2(S)-n-butyl-sulfonylamino)propionic acid]carboxamide (1-10)

A solution of 1-8 (0.28 g) in CH$_3$OH (20 ml)/THF (20 ml) was treated with LiOH. H$_2$O (excess) in H$_2$O (20 ml) with stirring at room temperature for 4 hrs. The reaction mixture was concentrated and the residue was acidified with 1N KHSO$_4$ solution and extracted with EtOAc. The organic phase was dried (MgSO$_4$) and concentrated to give the desired acid 1-9. This was dissolved in EtOAc (20 ml), cooled to −30° C. and HCl (gas) was bubbled into this solution for 1 hr. This was allowed to warm to room temperature with stirring for 2 hrs. The solvent was then removed and the residue collected to provide pure 1-10.

$^1$H NMR (300 MHz, CD$_3$OD) δ0.86 (3H, t), 1.30 (6H, m), 1.72 (5H, m), 2.00 (3H, m), 3.00 (6H, m), 3.32 (2H, m), 3.58 (1H, dd), 3.82 (1H, dd), 4.32 (1H, m), 7.13 (1H, s), 7.86 (1H, s).

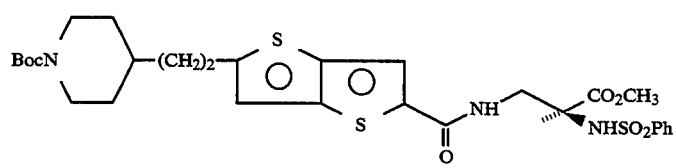

1-11

5-[2-(N-t-Butyloxycarbonylpiperidin-4-yl)ethyl]-thieno[3,2-b]-thiophene-2-N-[3-(methyl2(S)-phenylsulfonylamino)propionate]-carboxamide ( 1-11)

1-7 was treated with 2-7 as described for 1-8 to provide 1-11.

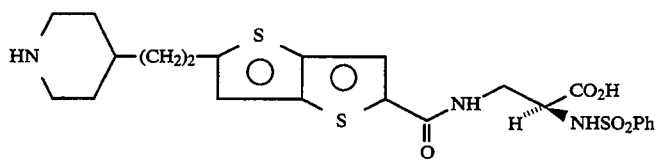

1-12

5-[2-(Piperidin-4-yl)ethyl]thieno[3,2-b]thiophene-2-N-[3-(2(S)-phenylsulfonylamino)propionic acid]carboxamide (1-12)

1-11 was treated with HCl gas in EtOAc as described for 1-10 to provide pure 1-12.

$^1$H NMR (300 MHz, CD$_3$OD) δ1.42 (3H, m), 1.72 (3H, m), 2.00 (3H, m), 2.98 (7H, m), 3.36 (3H, m), 3.71 (1H, dd), 4.15 (2H, m), 7.12 (1H,-s), 7.40 (3H, m), 7.69 (1H, s), 7.81 (2H, m).

5-[2-(Piperidin-4-yl)ethyl]thieno[3,2-b]thiophene-2-N-[3-(2(S)-benzylureido)propionic acid]carboxamide (1-4)

1-13 was treated with HCl gas in EtOAc as described for 1-10 to provide pure 2-14.

$^1$H NMR (300 MHz, CD$_3$OD) δ1.41 (2H, m), 1.70 (3H, m), 2.00 (2H, m), 2.98 (4H, m), 3.65 (2H, m), 4.38 (2H, m), 4.55 (1H, m), 7.16 (6H, m), 7.79 (1 H, s).

SCHEME 2

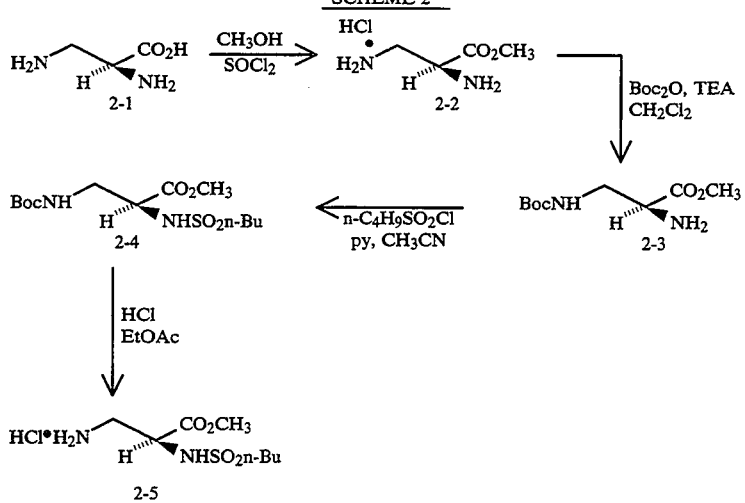

Methyl 2(S),3-diaminopropionate hydrochloride (2-2)

Methanol (400 mL) was cooled to 0° C. and thionyl chloride (217 mL, 3.0 moles, 20 eq) was added dropwise under argon. After addition was completed, the solution was warmed to RT for 20 min. 2(S),3-Diaminopropanoic acid (20 g, 0.143 mole) (Schweizerhall Chemicals) was crashed to a fine powder and added to the solution. The reaction was heated to reflux for 48 hrs, at which time TLC showed a small amount of starting material remaining. An additional portion of methanol (100 mL) and thionyl chloride (72 mL) was prepared as before and added to the reaction at RT; the

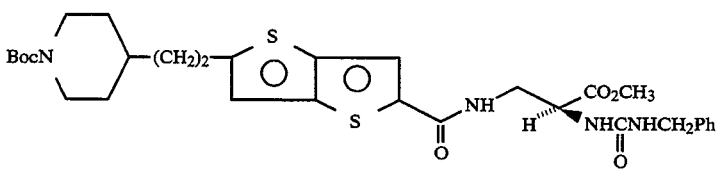

1-13

5-[2-(N-t-Butyloxycarbonylpiperidin-4-yl)ethyl]-thieno[3,2-b]thiophene-2-N-[3-(methyl2(S)-benzylureido)propionate]-carboxamide (1-13)

1-7 was treated with 2-9 as described for 1-9 to provide pure 1-13.

$^1$H NMR (300 MHz, CDCl$_3$) δ1.15 (2H, m), 1.45 (9H, s), 1.70 (3H, m), 2.65 (2H, t), 2.92 (2H,t), 3.75 (3H, s), 3.79 (2H, m) 4.10 (2H, bd), 4.32 (2H, m), 4.70 (1H, m), 6.93 (1H, s), 7.20 (5H; m), 7.61 (1H, s).

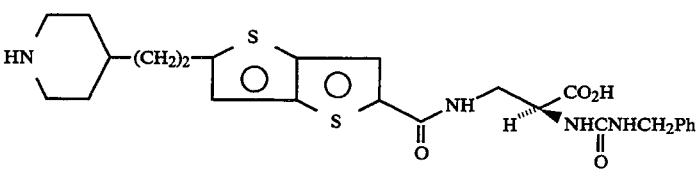

1-14 reaction was then stirred overnight at RT. The reaction was worked up by removal of solvent at 40° C. in vacuo to give 2-2as foam.

Rf 0.72 (9:1:1 EtOH/H2O/NH4OH). 1H NMR (400 MHz, D2O) δ4.55 (dd, J-5.4 8.2 Hz, 1H), 3.92 (s, 3H), 3.64 (dd, J-=8.2, 13.8 Hz, 1H), 3.55 (dd, J=5.4, 13.8 Hz, 1H).

Methyl [2(S)-amino-3-(N-t-Butyloxycarbonylamino]-propionate (2-3)

2-2(6.0 g, 31.5 mmole) was crashed to a fine powder, suspended in 1 L of CH2Cl2 and cooled to −78° C. under argon. Triethylamine (17.5 mL, 0.126 mole, 4 eq) was added dropwise as the solution gradually became homogenous. Di-t-butyldicarbonate (6.18 g, 2.83 mmole, 0.9 eq) was dissolved in 50 mL CH2Cl2 and added dropwise to the solution. After the addition was completed, the reaction was placed in an ice bath and stirred for 1 ½ hours. The reaction was transferred to a separatory funnel and extracted with 3×50 mL of 10% KHSO4 solution. The aqueous layer was washed with 3×10 mL of CH2Cl2, then basified with sat. NaHCO3 and 3N NaOH solution to pH10 and extracted with 10×100 mL of CH2Cl2. The organic layer was dried with Na2SO4, filtered and evaporated to give of a pale yellow oil. Column chromatography on silica gel with 2.5% MeOH/EtOAc gave 4.22 g (68%) of the pure product as an oil.

Rf 0.39 (5% MeOH/EtOAc). 1H NMR (400 MHz, CDCl3) δ5.0 (bs, 1H), 3.72 (s, 3H), 3.56 (t, J=5.7 Hz, 1H), 3.46 (m, 1H), 3.23 (m, 1H), 1.55 (bs, 2H), 1.42 (s, 9H).

Methyl [2(S)-(n-Butylsulfonylamino)-3-(t-butyloxycarbonylamino)]-propionate (2-4)

2-3 (2.5 g, 11.4 mmole) was dissolved in acetonitrile (100 mL) and three portions of n-butylsulfonyl chloride (1.62 mL, 12.5 mmole, 1.1 eq each) and pyridine (1.0 mL, 12.5 mmole, 1.1 eq each) were added over a period of three hours. The reaction was allowed to stir overnight, concentrated to ¼ its original volume, then diluted with 100 mL EtOAc and washed with 10% KHSO4 (5×20 mL), dried with brine and MgSO4, filtered and evaporated. Column chromatography on silica gel eluting with 20%–40% EtOAc/Hexanes gave the pure product as an oil.

Rf 0.6 (5% MeOH/CHCl3). 1H NMR (400 MHz, CDCl3) δ5.48 (bd, 1H), 4.9 (bs, 1H), 4.22 (m, 1H), 3.8 (s, 3H), 3.53 (m, 2H), 3.02 (m, 2H), 1.80 (m, 2H), 1.46 (m, 2H), 1.43 (s, 9H), 0.94 (t, J=7.4 Hz, 3H).

Methyl [2(S)-(n-Butylsulfonylamino)-3-amino]-propionate (2-5)

2-4 (2.0 g, 5.9 mmole) was dissolved in 30 mL of EtOAc and cooled to −40° C. HCl gas was bubbled through the solution until it was saturated, then the reaction was warmed to 0° C. and stirred for 1 hr. The excess HCl was removed under vacuum at room temperature and the reaction was concentrated at 35° C. to give pure product as a foam.

Rf 0.6 (9:1 EtOH/H2O). 1H NMR (400 MHz, CDCl3) δ8.1 (bs, 2H), 7.2 (m, 1H), 4.65 (m, 1H), 3.82 (s, 3H), 3.65 (m, 1H), 3.54 (m, 1H), 3.20 (bs, 2H), 1.8 (m, 2H), 1.45 (m, 2H), 0.95 (t, J=7.3 Hz).

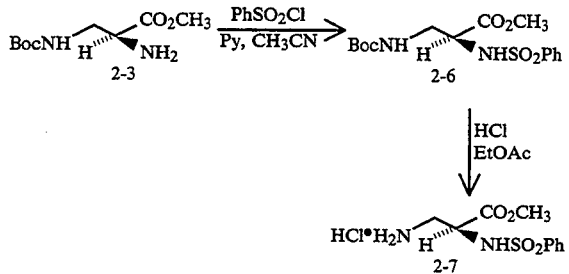

Methyl [2(S)-(Phenylsulfonylamino)-3-(t-butyloxycarbonylamino)]propionate (2-6)

Treatment of 2-3 (0.58 g, 2.67 mmol) in CHCl3 (10 ml) with PhSO2Cl (9.15 mmol) as described for 2-4 gave 2-6 following purification on silica gel eluting with 30% EtOAc/hexane (Rf 0.4). 1H NMR (300 MHz, CDCl3) δ1.45 (9H, s), 3.60 (3H, s), 4.03 (1H, m), 4.98 (1H, m), 6.70 (1 H, bd), 7.58 (3H, m), 7.89 (2H, d).

Methyl [2(S)-(Phenylsulfonylamino)-3-amino]propionate hydrochloride (2-7)

2-6 (0.8 g, 2.2 mmol) was dissolved on EtOAc (10 ml) and treated with HCl gas as described for 2-5to afford pure 2-7. Rf 0.4 [silica, 10% MeOH/CHCl3 (saturated NH4OH)].

1H NMR (300 MHz, CD3OD) δ3.09 (1H m), 3.30 (2H, m), 3.36 (1H, m), 3.40 (3H, s), 4.24 (1H, m), 7.60 (3H, m), 7.88 (2H, m).

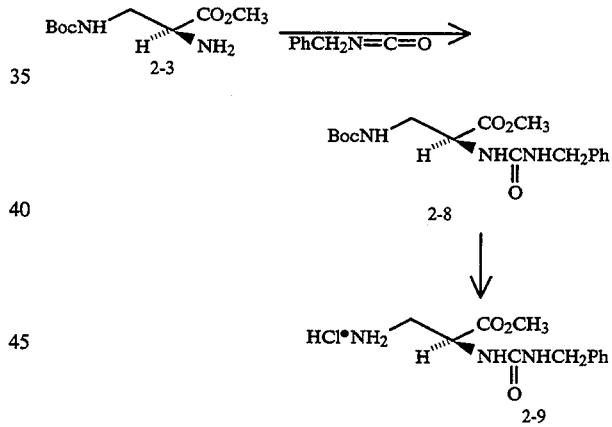

Methyl [2(S)-(Benzylureido)-3-(t-butyloxycarbonylamino)]propionate(2-8 )

2-3 (1.29 g, 5.91 mmol) in THF (35 ml) at room temperature was treated with benzyl isocyanate (6.5 mmol) with stirring for 16 hrs. The solvent was then removed and the residue was purified by flash chromatography on silica gel eluting with 5% MeOH/EtOAc to give pure 2-8.

1H NMR (3.00 MHz, CDCl3) δ1.43 (9H, s), 1.48 (2H, m), 3.40 (1H, m), 3.58 (1H, m), 3.63 (3H, s), 4.34 (3H, m), 4.57 (1H, m), 5.28 (1H, m), 5.47 (1H, m), 5.80 (1H, d), 7.26 (5H, m).

Methyl 2(S)-(Benzylureido)-3-aminopropionate hydrochloride (2-9)

2-8 (1.19 g) was dissolved in EtOAc and treated with HCl gas as described for 1-10 to provide pure 2-9.

1H NMR (300 MHz, CD3OD) δ3.25 (2H, m), 3.39 (2H, dd), 3.77 (3H, s), 4.35 (2H, s), 4.55 (1H, m), 7.35 (5H, m).

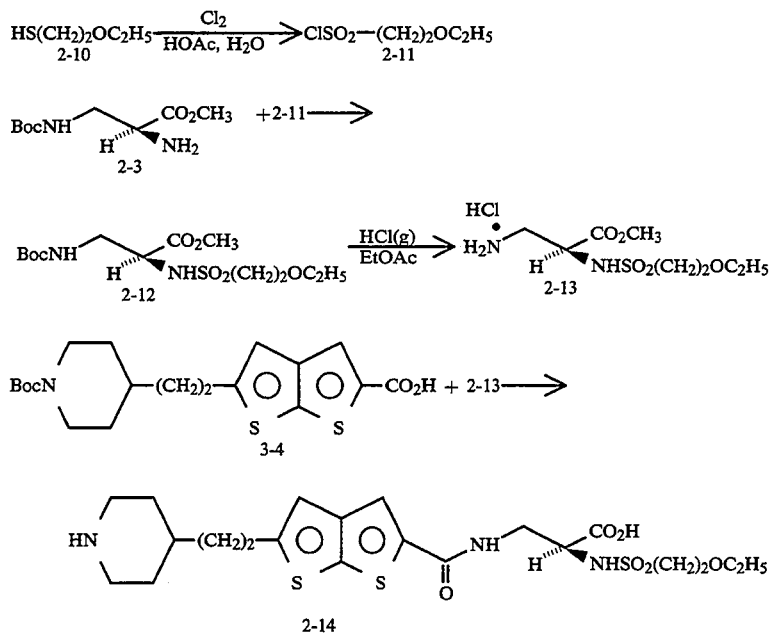

2-Ethoxyethanesulfonyl Chloride. (2-11)

A solution of HOAc(25 ml) and H$_2$O (2 ml) was cooled to 0° and treated with 2-mercaptoethyl ethyl ether (2-10) (4.5 ml, 47 mmol). A stream of chlorine gas was then bubbled into this solution for 2 minutes which mined from colorless to bright yellow. This solution was stirred at 0° for 3.5 hours, diluted with H$_2$O and extracted with CH$_2$Cl$_2$. The organic phase was washed with H$_2$O, 5% NaOH, H$_2$O, brine and dried (MgSO$_4$). Solvent removal gave 2-11 as a clear oil.

$^1$H NMR (300 MHz, CDCl$_3$) δ1.22 (3H, t), 3.78 (2H, q), 3.98 (4H, m).

Methyl [2(S)-(2-Ethoxyethanesulfonylamino)-3-(t-butyloxycarbonylamino)]propionate (2-12)

2-3 was treated with 2-11 as described for 2-4 to provide 2-12.

$^1$H NMR (300 MHz, CDCl$_3$) δ1.25 (3H, t), 1.45 (9H, s), 3.32 (2H, m), 3.5 (4H, m), 3.80 (3H, s), 3.84 (2H, m), 4.24 (1H, m).

Methyl [2(S)-(2-Ethoxyethanesulfonylamino)-3-amino]propionate (2-13)

2-12 was treated with HCl gas as described for 2-5 to give pure 2-13.

$^1$H NMR (300 MHz, CD$_3$OD) δ1.19 (3H, t), 3.65–3.76 (6H, m), 3.89 (5H, m).

5-[2-(Piperidin-4-yl)ethyl]thieno-[2,3-b]thiophene-2-N-[3-2(S)-(2-ethoxyethanesulfonylamino)propionic acid]-carboxamide (2-14)

3-4 was treated with 2-13 and this intermediate was deprotected as described for 1-10 to give pure 2-14.

$^1$H NMR (300 MHz, D$_2$O) δ1.03 (3H, t), 1.20–1.53 (5H, m), 1.75 (2H, bd), 2.60 (2H, bs), 2.73 (2H, bt), 3.34 (6H, m), 3.50 (1H, m), 3.75 (4H, m), 4.27 (1H, m), 6.80 (1H, s), 7.62 (1H, s).

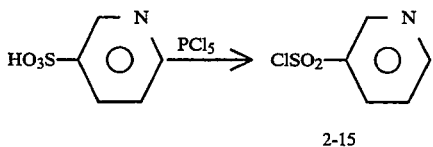

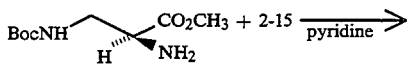

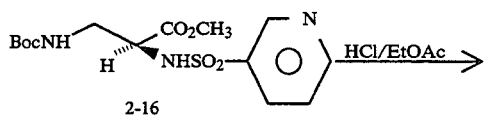

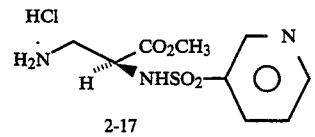

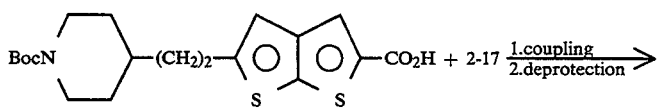

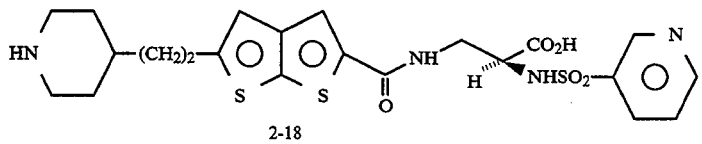

3-Pyridylsulfonyl chloride (2-15)

3-pyridylsulfonic acid (30 g, 0.188 mole) was added to PCl$_5$ (46.8 g, 0.225 mole), suspended in 150 mL toluene and heated to reflux overnight. The suspension was cooled and concentrated to yield a yellow oil, which was diluted with benzene, filtered through a pad of celite and concentrated to give 30.7 g (92%) of 2-15 as a yellow oil, which was used in the next step without purification.

$^1$H NMR (300 MHz, CDCl$_3$) δ9.27 (1H, s), 8.98 (1H, d, 8.35 (1H, d), 7.62 (1H, dd).

Methyl [2(S)-(3-Pyridylsulfonylamino)-3-(N-t-butyloxycarbonyl)amino]propionate (2-16)

Methyl 2(S)-amino-3-(N-t-butyloxycarbonyl)aminopropionate 2-3 (16.8 g, 0.077 mole) dissolved in 330 mL methylene chloride was treated with sulfonyl chloride 2-15 (20.6 g, 0.116 mole) and pyridine (12.5 mL, 0.154 mole) and the reaction was stirred for 21 hours. The reaction was concentrated, absorbed to silica and chromatographed with a gradient of 30%-70%. acetone/hexanes to give crude 2-16 which was swished with hot EtOAc, cooled and filtered to give 2-16 as a pale yellow solid. R$_f$0.29 (30% acetone/hexanes).

$^1$H NMR (300 MHz, CDCl$_3$) δ9.0 (1H, s), 8.8 (1H, d), 8.6 (1H, d), 8.1 (1H, d), 7.45 (1H, dd), 7.3 (1H, m), 4.1 (1H, m), 4.1 (3H, s), 3.4–3.5 (2H, m), 1.4 (9H, s).

Methyl [2(S)-(3-Pyridylsulfonylamino)-3-amino]propionate (2-17)

Methyl 2(S)-(3-pyridylsulfonyl)amino-3-(N-t-butyloxycarbonyl) aminopropionate 2-16(17.5 g, 0.049 mole) was suspended in 200 mL EtOAc and cooled to −78° C. HCl gas was bubbled through the solution for ten minutes and the solution was then placed in an ice bath. After stirring for 40 minutes at 0° C., no starting material could be detected by TLC. The solution was concentrated, first at room temperature, then at 40° C. to yield 2-17 as an off-white solid. R$_f$0.34 (9:1:1 EtOH/-H$_2$O/NH$_4$OH).

$^1$H NMR (300 MHz, CD$_3$OD) δ9.3 (1H, s), 9.0 (1H, dd), 8.9 (1H, d), 8.2 (1H, dd), 4.6 (1H, dd), 3.6 (3H, s), 3.5 (1H, dd), 3.3 (1H, dd).

5-[2-(Piperidin-4-yl)ethyl]thieno[2,3-b]thiophene-2-N-[3-2(S)-(3-pyridylsulfonylamino)propionic acid] carboxamide (2-18)

3-4 was treated with 2-17 and the resulting intermediate was deprotected as described for 1-10 to provide 2-8.

$^1$H NMR (300 MHz, D$_2$O) δ0.85 (2H, m), 1.07 (1H, m), 1.34 (4H, m), 2.22 (2H, t), 2.35 (2H, m), 2.38 (2H, bd), 3.06 (1H, t), 3.62 (2H, m), 6.80 (1H, s) 6.92 (1H, m), 7.24 (1H, s), 7.79 (1H, d), 7.97 (1H, dd), 8.70 (1H, d).

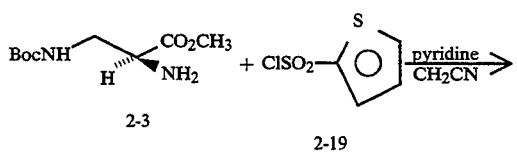

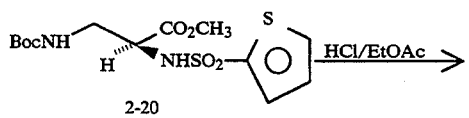

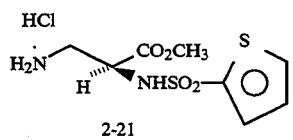

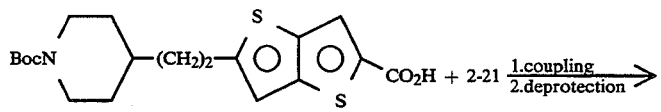

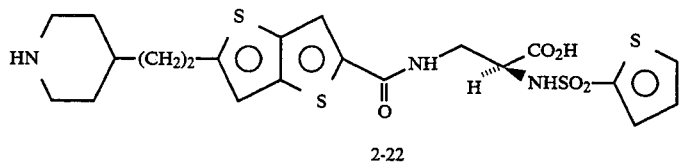

Methyl [2(S)-(2-Thienylsulfonylamino-3-(N-t-butyloxycarbonyl)amino]propionate (2-20)

A solution of 2-3 (1.76 g, 5 mmol) in CH₃CN (15 ml) was treated at room temperature with pyridine (6 mmol) and 2-thiophenesulfonyl chloride (1.0 g, 5.5 mmol) (Aldrich) and this was stirred for 4 hours. The reaction mixture was concentrated, taken up in H₂O/EtOAc and the organic phase was washed with 10% KHSO₄, brine and dried. Solvent removal gave a residue that was purified by flash chromatography on silica gel eluting with hexane (7)-EtOAc (3) to give pure 2-20. R$_f$0.25 [silica, hexane (7)-EtOAc(3)].

Methyl [2(S)-(2-Thienylsulfonylamino)-3-amino]propionate (2-21)

2-20 was dissolved in EtOAc and treated with HCl gas as described for 2-17 to provide pure 2-21.

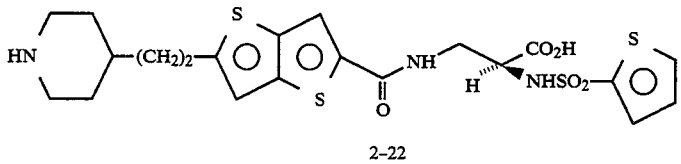

5-[2-(Piperidin-4-yl)ethyl]thieno[3,2-b]thiophene-2-N-[3-(2(S)-(2-thienylsulfonylamino) propionic acid] carboxamide (2-22)

1-7 was treated with 1-21 as described for 1-8 and this intermediate was deprotected sequentially with LiOH and HCl/EtOAc, as described for 1-10, to provide 2-22.

¹H NMR (300 MHz, CD₃OD) δ1.45 (2H, m), 1.75 (3H, m), 2.08 (3H, m), 2.95 (4H, m), 3.37 (3H, m), 3.52 (1H, dd), 3.75 (1H, dd), 4.24 (1H, m), 6.98 (1H, m), 7.13 (1H, s), 7.58 (2H, m), 7.76 (1H, s).

SCHEME 3

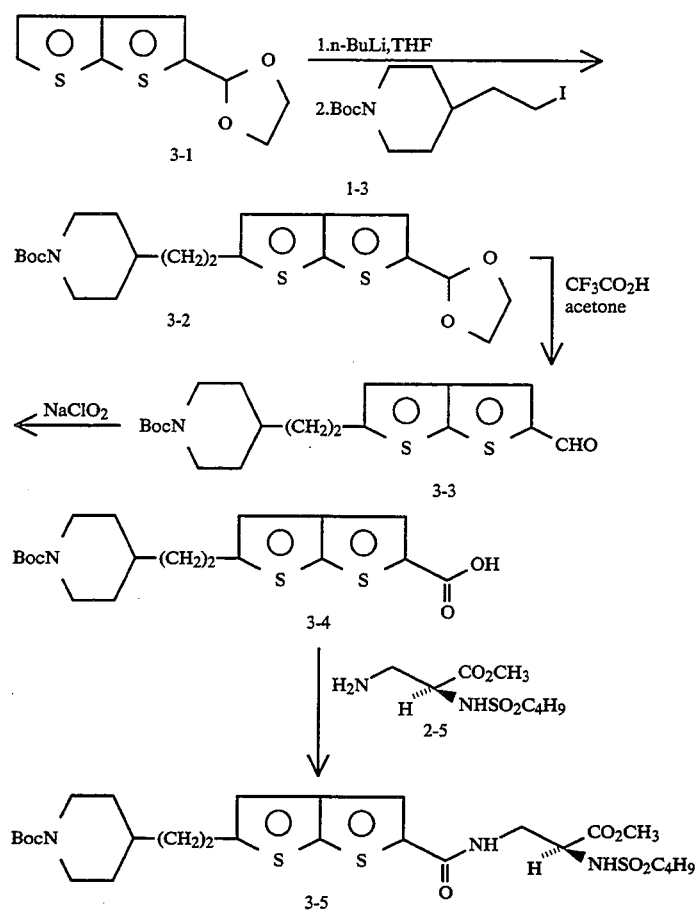

-continued
SCHEME 3

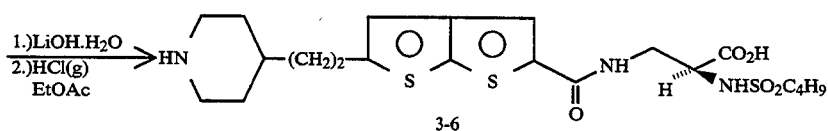

5-[2-(N-t-Butyloxycarbonylpiperidin-4-yl)ethyl]-thieno[2,3-b]thiophene-2-carboxaldehyde ethylene glycol acetal (3-2)

Treatment of 3-1 (J. D. Prugh, et al. *J. Med. Chem.* 1991, 34, 1805–1818) (0.212 g, 1.0 mmol) with n-BuLi (1.0 mmol) followed by 1-3 (0.34 g, 1.0 mmol) as described for 1-5 provided crude 3-2. This was purified by flash chromatography on silica gel eluting with 10% EtOAc/hexanes to give pure 3-2.

$^1$H NMR (300 MHz, CD$_3$OD) δ1.15 (2H, m), 1.45 (9H, s), 1.68 (4H, m), 2.67 (2H, t), 2.90 (2H, t), 4.10 (4H, m), 6.14 (1H, s), 6.87 (1H, s), 7.21 (1H, s).

5-[2-(N-t-Butyloxycarbonylpiperidin-4-yl)ethyl]-thieno[2,3-b]thiophene-2-carboxaldehyde (3-3)

3-2 (2.36 g, 5.57 mmol) was treated with trifluoroacetic acid (6.6 ml) in acetone (60 ml) at room temp as described for 1-6 to provide 3-3 an oil.

$^1$H NMR (300 MHz, CD$_3$OD) δ1.15 (2H, m), 1.45 (9H, s), 1.68 (4H, m), 2.68 (2H, t), 2.93 (2H, t), 4.10 (2H, bd), 7.00 (1H, s), 7.77 (1H, s), 9.90 (1H, s).

5-[2-(N-t-Butyloxycarbonylpiperidin-4-yl)ethyl]-thieno[2,3-b]thiophene-2-carboxylic acid (3-4)

3-3 (2.0 g, 5.27 mmol) was treated with NaClO$_2$ (5.27 g, 58.3 mmol) as described for 1-7 to provide 3-4 as a white solid.

5-[2-(Piperidin-4-yl)ethyl]thieno[2,3-b]-thiophene-2-N-[3-(2(S)-n-butylsulfonylamino)propionic acid]carboxamide (3-6)

3-5 was treated with LiOH. H$_2$O as described for 1-8 to provide the desired acid. This was dissolved in EtOAc and treated with HCl gas as described for 1-10 to provide pure 3-6.

$^1$H NMR (300 MHz, CD$_3$OD) δ0.85 (3H, t), 1.48 (4H, m), 1.72 (4H, m), 2.00 (2H, bd), 3.00 (3H, m), 3.56 (1H, m), 3.82(1H, m), 4.30 (1H, m), 7.05 (1H, s), 7.76 (1H, s).

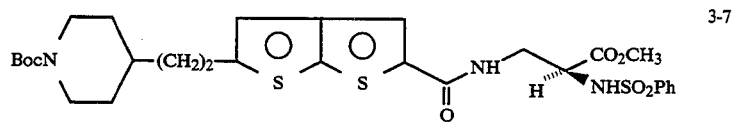

5-[2-(N-t-Butyloxycarbonylpiperidin-4-yl)ethyl]-thieno[2,3-b]thiophene-2-N-[3-(methyl-2(S)-phenylsulfonylamino)-propionate]carboxamide (3-7)

3-4 (0.2 g, 0.5 mmol) was treated with methyl 2(S)-phenylsulfonylamino-3-diaminopropionate (2-7) (0.15 g, 0.5 mmol), HOBT (0.074 g, 0.55 mmol), EDC (0.11 g, 0.58 mmol), and NMM (0.15 mmol as described for 1-8 to provide crude 3-7. This was purified by flash chromatography on silica gel eluting with 55% EtOAc/hexanes to give pure 3-7.

$^1$H NMR (300 MHz, CD$_3$OD) δ1.15 (2H, m), 1.45 (9H, s), 1.69 (4H, m), 2.69 (2H, t), 2.90 (2H, t), 3.62 (3H, s), 3.91 (1H, m), 4.10 (3H, m), 5.81 (1H, d), 6.70 (1H, m), 6.90 (1H, s), 7.50 (4H, m), 7.85 (2H, dd).

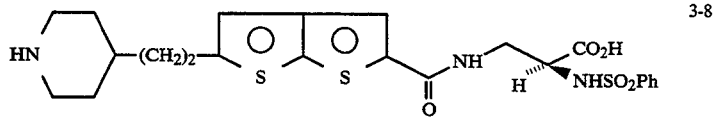

$^1$H NMR (300 MHz, CD$_3$OD) δ1.17 (2H, m), 1.46 (9H, s), 1.70 (4H, m), 2.68 (2H, t), 2.92 (2H, t), 4.10 (2H, bd), 6.95 (1H, s), 7.94 (1H, s).

5-[2-(N-t-Butyloxycarbonylpiperidin-4-yl)ethyl]-thieno[2,3-b]thiophene-2-N-[3-(methyl2(S)-n-butylsulfonylamino)propionate]-carboxamide (3-5)

3-4 (0.20 g, 0.5 mmol) was treated with 2-5(0.14 g, 0.5 mmol), HOBT (0.07 g, 0.55 mmol), EDC (0.11 g, 0.58 mmol), and NMM (0.15 g, 1.5 mmol) in DMF (10 ml) as described for 1-8 to provide 3-5 after chromatography on silica gel eluting with 55% EtOAc/hexane (R$_f$0.3).

5-[2-(Piperidin-4-yl)ethyl]thieno[2,3-b]thiophene-2-N-[3-(2(S)-phenylsulfonylamino) propionic acid]carboxamide (3-8)

3-7 was treated with LiOH. H$_2$O in CH$_3$OH/H$_2$O as described for 1-8 to provide the derived acid. This was dissolved in EtOAc, cooled to 10° and treated with HCl (gas) as described for 1-10 to provide pure 3-8 after trituration with water.

$^1$H NMR (300 MHz, DMSO-d) δ1.30 (2H, m), 1.58 (3H, m), 1.82 (2H, d), 2.80 (4H, m), 3.20 (3H, m), 7.14 (1H, s), 7.49 (3H, m), 7.79 (3H, m), 8.61 (2H, m).

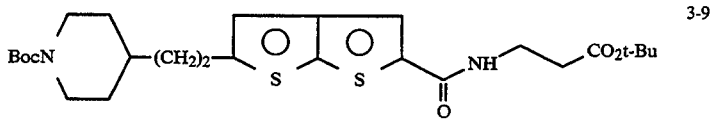

5-[2-(N-t-Butyloxycarbonylpiperidin-4-yl)ethyl]-thieno[2,3-b]thiophene-2-N-[3-(t-butyl propionate)]carboxamide (3-9)

3-9 (0.1 g, 0.25 mmol) was treated with t-butyl β-alanine (0.045 g, 0.25 mmol), HOBT (0.037 g, 0.275 mmol), EDC (0.056 g, 0.29 mmol), and NMM (0.076 g, 0.75 mmol) in DMF (5 ml) as described for 1-8 to provide crude 3-9. This was purified by flash chromatography on silica gel eluting with 40% EtOAc/hexane to give pure 3-9.

¹H NMR (300 MHz, CDCl₃) δ1.17 (2H,m), 1.45 (9H, s), 1.47 (9H, s), 1.67 (4H, m), 2.55 (2H, t), 2.68 (2H, t), 2.91 (2H, t), 3.68 (2H, q), 4.10 (2H, bd), 6.72 (1H, m), 6.96 (1H, s), 7.60 (1H, s).

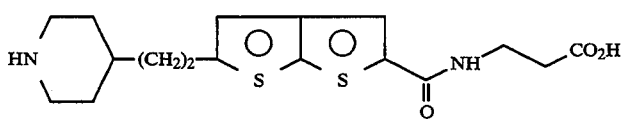

5-[2-(Piperidin-4-yl)ethyl]thieno[2,3-b]thiophene-2-N-[3-propionic acid]carboxamide (3-10).

3-9 was treated with HCl gas in EtOAc as described for 1-10 to provide pure 3-10.

¹H NMR (300 MHz, CD₃OD) δ1.42 (2H, m), 1.73 (2H, m), 2.0 (2H, m), 2.62 (2H, t), 2.92 (4H, m), 3.48 (2H, bd), 3.60 (2H, t), 7.13 (1H, s), 7.82 (1H, s).

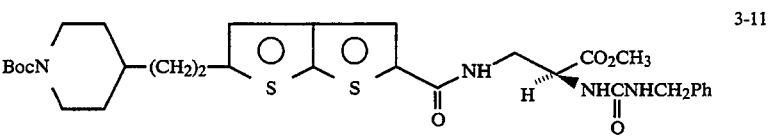

5-[2-(N-t-Butyloxycarbonylpiperidin-4-yl)ethyl]-thieno[2,3-b]-thiophene-2-N-[3-(2(S)-benzylureido)propionate]carboxamide (3-11)

3-4 was treated with 2-9 as described for 1-8 to provide pure 3-1.

¹H NMR (300 MHz, CDCl₃) δ1.13 (2H, m), 1.45 (9H, s), 1.68 (3H, m), 2.68 (2H, t), 2.90 (2H, t), 4.10 (2H, bd), 4.30 (2H, m), 4.71 (1H, m), 6.86 (1H, s), 7.22 (5H, s), 7.55 (1H, s).

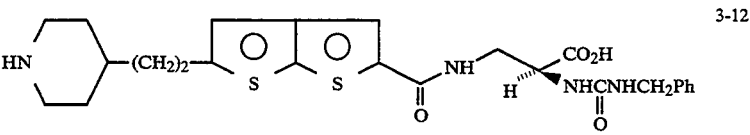

5-[2-(Piperidin-4-yl)ethyl]thieno[2,3-b]thiophene-2-N-[3-(2(S)-benzylureido)propionate]carboxamide (3-12)

3-11 was dissolved in EtOAc and treated with HCl gas as described for 1-10 to provide pure 3-12.

¹H NMR (300 MHz, CD₃OD) δ1.40 (2H, m), 1.72 (3H, m), 2.00 (3H, m), 2.96 (2H, m), 3.45 (2H, bd), 3.71 (2H, m), 7.03 (1H, s), 7.18 (5H, m), 7.71 (1H, s).

SCHEME 4

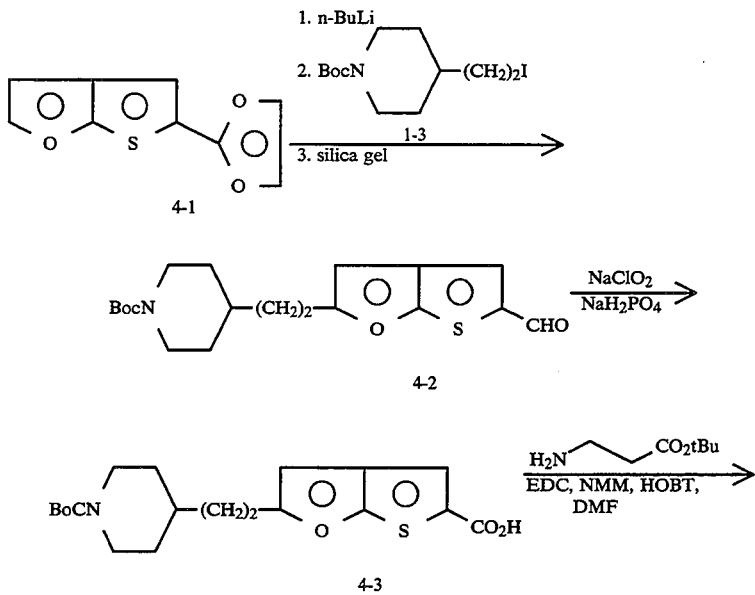

SCHEME 4

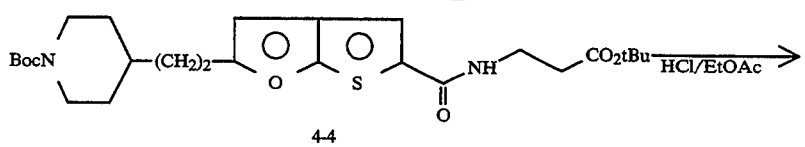

4-4

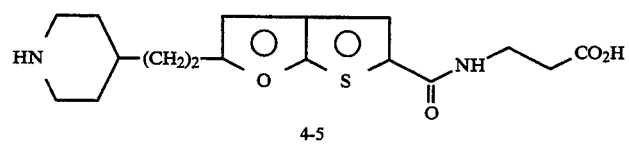

4-5

2-[2-(N-t-Butyloxycarbonylpiperidin-4-yl)ethyl]-thieno[2,3-b]furan-5-carboxaldehyde (4-2)

A solution of thieno[2,3-b]furan autal (4-1), (G. D. Hartman, et al. *J. Med. Chem.* 1992, 35, 3027) (3.92 g, 20 mmol) in THF (140 ml) was cooled to −75° and treated with n-BuLi (20 mmol). After stirring for 1 hour at −70° this was treated with HMPA (3.5 ml), followed by 1-3 (6.79 g, 20 mmol) with stirring at −70° for 3 hours and then at ambient temperature overnight. The reaction mixture was quenched with 10% $KHSO_4$ solution and the reaction mixture was concentrated. The residue was taken up in $Et_2O$, washed with $H_2O$, brine, dried ($Na_2SO_4$) and concentrated. This oil was purified by flash chromatography on silica gel eluting with hexane (88%) - EtOAc (12%) to give an oil which was triturated with hexane (9)-EtOAc(1) to give pure 4-2.

$^1$H NMR (300 MHz, $CDCl_3$) δ1.06–1.30 (2H, m), 1.45 (9H, s), 1.50–1.80 (5H, m) 2.60–2.75 (2H, dt), 2.75–2.83 (2H, t), 4.02–4.18 (2H, bd), 6.39 (1H, s), 7.59 (1H, s), 9.86 (1H, s).

2-[2-(N-t-Butyloxycarbonylpiperidin-4-yl)ethyl]-thieno[2,3-b]furan-5-carboxylic acid (4-3)

A solution of 4-2 (2.5 g, .6.9 mmol) in t-BuOH (200 ml) was treated with a solution of $NaClO_2$ (7.00 g, 77.4 mmol) and $NaH_2PO_4 \cdot H_2O$ (7.0 g, 50.7 mmol) in $H_2O$ (70 ml), followed by 30 ml of 2-methyl-2-butene. This 2-phase mixture was stirred at ambient temperature for 16 hours. The reaction mixture was diluted with EtOAc (250 ml) and the organic phase was separated and washed with 10% $KHSO_4$ solution, brine, dried and concentrated. The resulting residue was triturated with hexane to give 4-3.

$^1$H NMR (300 MHz, $CDCl_3$) δ1.06–1.29 (2H, m), 1.46 (9H, s), 1.46–1.8 (5H, m), 2.6–2.75 (2H, bt), 2.75–2.83 (2H, t), 4.01–4.20 (2H, bd), 6.36 (1H, s), 7.73 (1H, s), 8.8 (1H, vb).

2-[2-(N-t-Butyloxycarbonylpiperidin-4-yl)ethyl]-thieno-[2,3-b]furan-5-N-(3-t-butyl propionate)carboxamide (4-4)

4-3 was treated with β-alanine methyl ester as described for 1-8 to give pure 4-4 after chromatography on silica gel eluting with hexane (7)-EtOAc (3).

$^1$H NMR (300 MHz, $CDCl_3$) δ1.06–1.25 (2H, m), 1.47 (1H, s), 1.47–1.75 (5H, m), 2.50–2.60 (2H, t), 2.60–2.75 (2H, bt), 2.75– 2.81 (2H, t), 3.61–3.71(2H, q), 4.02–4.18 (2H, bd), 6.31 (1H, s), 6.68 (1H, bt), 7.29 (1H, s).

2-[2-(Piperdin-4-yl)ethyl]thieno[2,3-b]furan-5-N-(3-propionic acid)carboxamide (4-5)

4-4 was treated with HCl gas in EtOAc as described for 1-10 to provide 4-5.

$^1$H NMR (300 MHz, $CD_3OD$) δ1.35–1.52 (2H, m), 1.59–1.82 (3H, m), 1.95–2.07 (2H, bd), 2.58–2.65 (2H, t), 2.80–2.88 (2H, t), 2.88–3.13 (2H, dt), 3.32–3.45 (2H, bd), 3.55–3.65 (2H, m), 6.49 (1H, s), 7.52 (1H, s), 8.48 (<1H, bt).

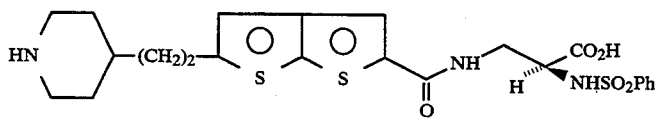

4-6

2-[2-(Piperidin-4-yl)ethyl]thieno[2,3-b]furan-5-N-[3-(2S)-phenylsulfonyl-aminopropionic acid]carboxamide (4-6)

4-6 was prepared from 4-3 and 2-6 in analogous fashion to 4-5.

$^1$H NMR (300 MHz, $CD_3OD$)δ1.30–1.51 (2H, m), 1.60–1.80 (3H, m), 1.95–2.07 (2H, bd), 2.80–2.90 (2H, t), 2.90–3.02 (2H, dt), 3.33–3.53 (3H, m), 3.66–3.75 (1H, m), 4.12–4.21 (1H, m), 6.50 (1H, s), 7.34–7.52 (4H, m), 7.79–7.87 (2H, d), 8.38–8.46 (>1H, bt)

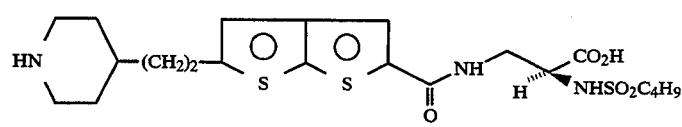

4-7

2-[2-(Piperidin-4-yl)ethyl]thieno[2,3-b]furan-5-N-[3-2(S)-butylsulfonylaminopropionic acid)]carboxamide (4-7)

4-7was prepared from 4-3 and 2-5in analogous fashion to 4-5.

$^1$H NMR (300 MHz, $CD_3OD$) δ0.82–0.92 (3H, t), 1.27–1.50 (4H, m), 1.60–1.90 (5H, m), 1.94–2.05 (2H, bd), 2.80–2.88 (2H, t), 2.88–3.10 (4H, m), 3.32–3.42 (2H, bd), 3.50–3.61 (1H, m), 3.75–3.85 (1H, m), 4.23–4.31 (1H, m), 6.50 (1H, s), 7.58 (1H, s), 8.46–8.53 (>1H, bt).

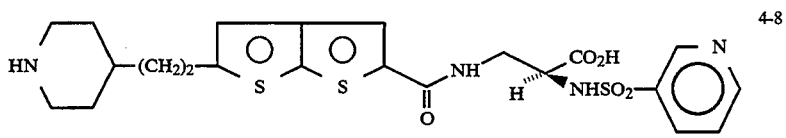

2-[2-(Piperidin-4-yl)ethyl]thieno[2,3-b]furan-5-N-[3-(2(S)-3-pyridylsulfonylaminoproponic acid)]carboxamide (4-8)

4-8 was prepared from 4-3 and 2-17 in analogous fashion to 4-5.

$^1$H NMR (300 MHz, CD$_3$OD) δ1.31–1.41 (2H, m), 1.60–1.81 (3H, m), 1.96–2.10 (2H, bd), 2.80–2.90 (2H, t), 2.90–3.03 (2H, dt), 3.33–3.43 (2H, bd) 3.47–3.56 (1H, dd), 4.74–4.83 (1H, dd), 4.35–4.42 (1H, m), 6.50 (1H, s), 7.49 (1H, s), 7.89–7.98 (1H, bt), 8.68–8.78 (1H, bd), 8.78–8.85 (1H, d), 9.19 (1H, bd).

SCHEME 5

5-[2-(N-t-Butyloxycarbonylpiperidin-4-yl)ethyl]-thieno[2,3-b]thiophene-2-carboxylic acid (3-4)

A solution of 5-1 (0.184 g, 1 mmol) (J. D. Prugh, et al. *J. Med. Chem.* 1991, 34, 1805–18) in THF (7 ml) was treated with HMPA (0.72 g, 4 mmol), cooled to −78° for 0.5 hr., and then treated with a solution of 1-3 (0.34 g, 1.0 mmol) in THF (2 ml). The resulting solution was stirred at −70° for 3 hours and then at ambient temperature overnight. The reaction mixture was concentrated and the residue was partitioned between EtOAc and 1N KHSO$_4$ solution. The organic phase was separated, washed with water, brine, dried (MgSO$_4$) and concentrated. The residue was triturated with hexane to provide 3-4.

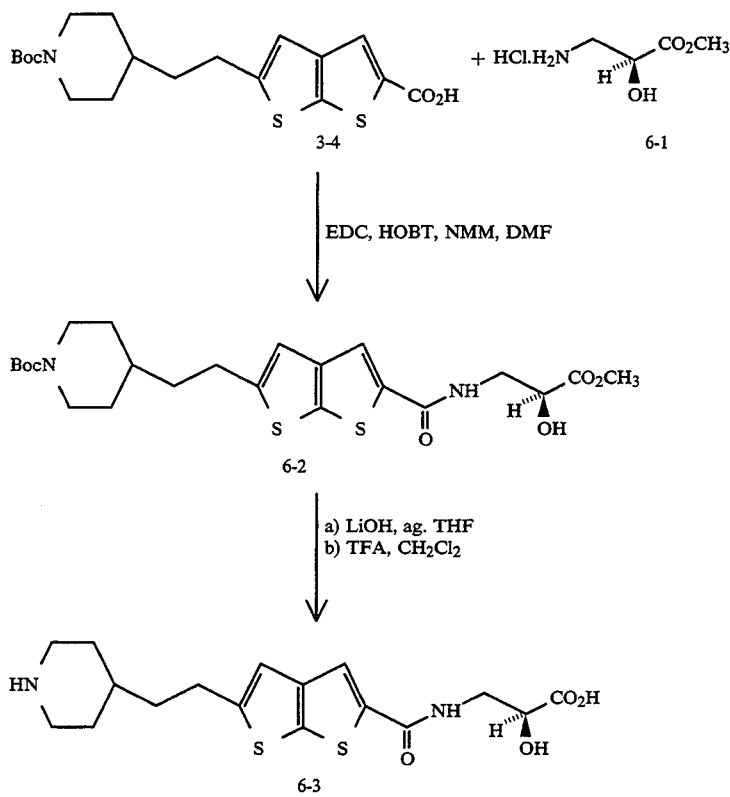

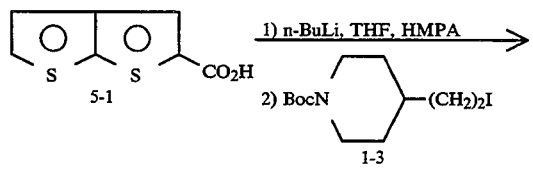

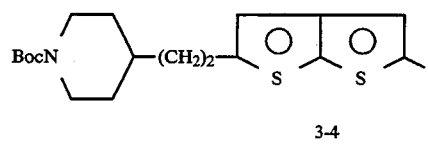

5-[2-(N-t-Butyloxycarbonylpiperidin-4-yl)ethyl]-thieno[2,3-b]-thiophene-2-N-[3-(methyl2(S)-hydroxypropionate]carboxamide (6-2)

A stirred solution of 3-4 (80 mg, 0.20 mmol), 6-1 (for preparation see *Pol. J. Chem.* 53 (7-8), 1533, 1993) (38 mg, 0.24 mmol), HOBT (35 mg, 0.25 mmol), NMM (77 μL, 0.70 mmol), and DMF (2 mL) at −15° was treated with EDC (50 mg, 0.25 mmol) in a single portion followed by removal of the cooling bath. After 20 hours the reaction mixture was diluted with EtOAc and then washed with 10% KHSO$_4$, saturated NaHCO$_3$, H$_2$O, brine, dried (MgSO$_4$) and concentrated. Flash chromatography (silica, 80% EtOAc/hexanes) gave 6-2 as a white solid.

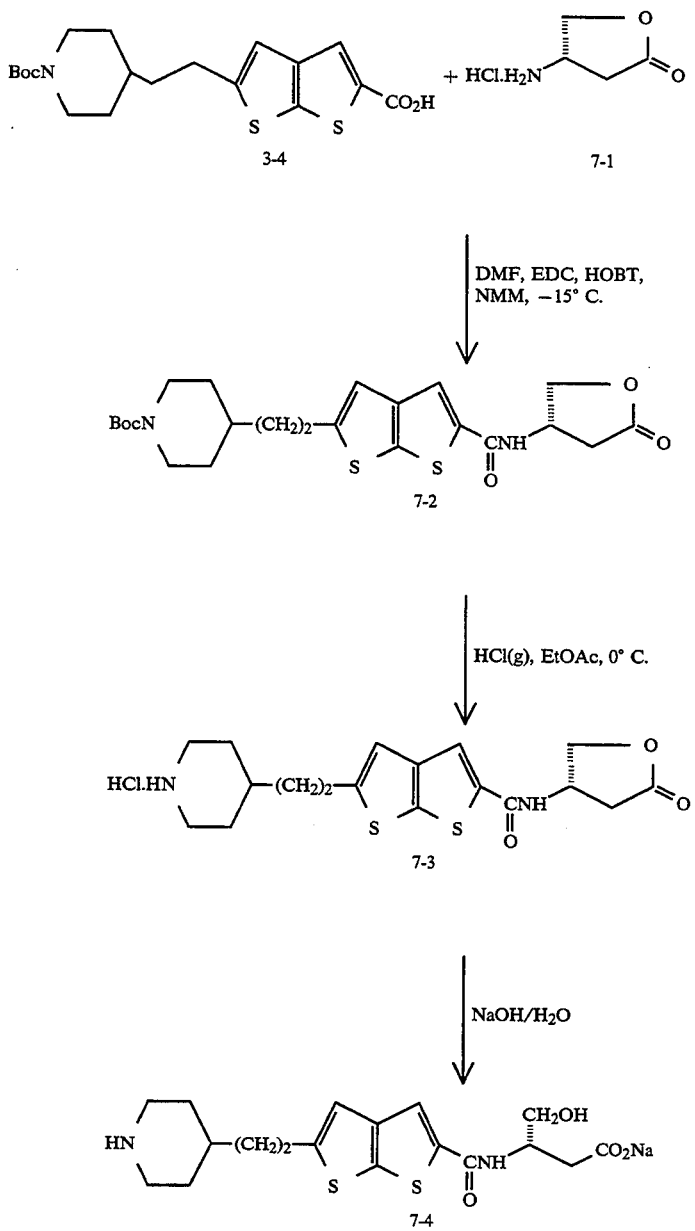

$^1$H NMR (400 MHz, CDCl$_3$) δ1.14 (m, 2H), 1.46 (9H, s), 1.45–1.74 (5H, m), 2.67 (2H, m), 2.91 (2H, bt), 3.92 (1H, m), 3.80 (2H, m), 3.83 (3H, s), 4.09 (2H, m), 4.40 (1H, m), 6.38 (1H, m), 6.91 (1H, s), 7.53 (1H, s).

5-[2-(Piperidin-4-yl)ethyl]thieno[2,3-b]thiophene-2-N-[3-(2(S)-hydroxypropionic acid)]carboxamide (6-3)

To a stirred solution of 6-2 (78 mg, 0.16 mmol) in THF (1.6 ml) was added 1N LiOH (0.4 ml, 0.4 mmol). After 2.5 hours the reaction mixture was diluted with EtOAc and washed sequentially with 10% KHSO$_4$, and brine, and then concentrated. The resulting white solid was dissolved in CH$_2$Cl$_2$ (0.8 ml) and then treated with TFA (0.8 ml). After 1 hour the reaction was concentrated and the residual TFA removed with toluene. Trituration of the resulting oil with 10:1:1 ethanol/N-H$_4$OH/H$_2$O gave 6-3 as a colorless solid after filtration.

$^1$H NMR (400 MHz, D$_2$O) δ1.23 (2H, m), 1.47 (1H, m), 1.53 (2H, m), 1.70 (2H, m), 2.73 (4H, m), 3.22 (2H, m), 3.57 (2H, d), 4.32 (1H, t), 6.80 (1H, s), 7.58 (1H, s).

5-[2-(N-t-Butoxycarbonylpiperidin-4-yl)ethyl]-thieno[2,3-b]thiophene-2-N-[4(S)-furanone]carboxamide (7-2)

Utilizing the procedure for converting 3-4 to 6-2, 3-4 (100 mg, 0.25 mmol) was coupled to 7-1 (for preparation see: Hvidt, T. et al., Can. J. Chem., 66(4), 779, 1988; 41 mg, 0.30 mmol) to afford 7-2 (120 mg) as a white solid after flash chromatography (silica, 75% EtOAc/hexanes).

$^1$H NMR (400 MHz, CDCl$_3$) δ1.13 (2H, m), 1.46 (9H, s), 1.45–1.70 (5H, m), 2.64 (3H, m), 2.86 (2H, m), 2.95 (1H, m), 4.08 (2H, m), 440 (1H, m), 4.59 (1H, m), 4.92 (1H, m), 6.88 (1H, s), 7.41 (1H, bd), 7.64 (1H, s).

5-[2-(Piperidin-4-yl)ethyl]thieno[2,3-b]thiophene-2-N-[4(S)-furanone]carboxamide (7-3)

7-2 (119 mg, 0.25 mmol) was dissolved in EtOAc and treated with HCl gas as described for 2-17 to provide 7-3 (93 mg) as a colorless solid.

$^1$H NMR (400 MHz, D$_2$O) δ1.27 (2H, m), 1.50 (1H, m), 1.57 (2H, m), 1.83 (2H, m), 2.58 (1H, dd), 2.79 (4H, m), 2.97 (1H, dd), 3.26 (2H, m), 4.30 (1H, dd), 6.92 (1H, s), 7.60 (1H, s).

5-[2-(Piperidin-4-yl)ethyl]thieno[2,3-b]thiophene-2-N-[3(S)-hydroxy-methyl(sodium)propionate]carboxamide (7-4)

7-3 (21 mg, 45 μg) was dissolved in 50 mM NaOH (4.55 ml). After 1 hour the solution was concentrated to dryness to give 7-4 as a solid.

$^1$H NMR (400 MHz, D$_2$O) δ0.90 (2H, m), 1.13 (1H, m), 1.36 (2H, m), 1.45 (2H, m), 2.32 (4H, m), 2.60 (2H, m), 2.80 (2H, m), 3.54 (2H, m), 4.28 (1H, m), 6.82 (1H, s)

The term "pharmaceutically acceptable salts" shall mean non-toxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

The term "pharmaceutically effective amount" shall mean that amount of a drug or pharmaceutical agent that will elicit the biological or medical response of a tissue, system or animal that is being sought by a researcher or clinician. The term "anticoagulant" shall include heparin, and warfarin. The term "thrombolytic agent" includes agents such as streptokinase and tissue plasminogen activator. The term "platelet anti-aggregation agent" includes such as aspirin and dipyridamole.

The term "alkyl" means straight or branched alkane, alkene or alkyne. The term "alkoxy" includes an alkyl portion where alkyl is as defined above. The terms "arylalkyl" and "alkylaryl" include an alkyl portion where alkyl is as defined above and to include an aryl portion where aryl is as defined above. The C$_{0-n}$ or C$_{1-n}$ designation where n may be an integer from 1–10 or 2–10 respectively refers to the alkyl component of the arylalkyl or alkylaryl unit. The term "halogen" includes fluorine, chlorine, iodine and bromine. The term "oxy" means an oxygen (O) atom. The term "thio" means a sulfur (S) atom. Under standard nomenclature used throughout this disclosure, the terminal portion of the designated side chain is described first followed by the adjacent functionality toward the point of attachment. For example, a C$_{1-6}$ alkyl substituted with C$_{1-6}$ alkylcarbonylamino is equivalent to

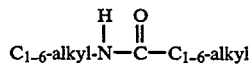

In the schemes and examples below, various reagent symbols have the following meanings:

| | |
|---|---|
| BOC (or Boc): | t-butyloxycarbonyl. |
| Pd-C: | Palladium on activated carbon catalyst. |
| DMF: | Dimethylformamide. |
| DMSO: | Dimethylsulfoxide. |
| TFA: | trifluoroacetic acid. |
| CBZ: | Carbobenzyloxy. |
| CH$_2$Cl$_2$: | Methylene chloride. |
| CHCl$_3$: | chloroform. |
| EtOH: | ethanol. |
| MeOH: | methanol. |
| EtOAc: | ethyl acetate. |
| HOAc: | acetic acid. |
| BOP: | Benzotriazol-1-yloxytris(dimethylamino)-phosphonium, hexafluorophosphate. |
| EDC: | 1-(3-Dimethylaminopropyl)-3-ethylcarbodiimide. |
| Oxone: | potassium peroxymonosulfate. |
| LDA: | Lithium diisopropylamide. |

The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. The compounds of the present invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., Amer. J. Physiol.,252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarilly skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.1–100 mg/kg/day and most preferably 0.1–20 mg/kg/day. Intravenously, the most preferred doses will range from about 1 to about 100 µg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittant throughout the dosage regime.

In the methods of the present invention, the compounds herein described in detail can form the active ingredient, and are typically administered in admixture with suitable pharmaceutical diluents, excipients or carders (collectively referred to herein as "carder" materials) suitably selected with respect to the intended form of administration, that is, oral tablets, capsules, elixers, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium sterate, dicalcium phosphate, calcium sulfate, mannitol, sorbitol and the like; for oral administration in liquid form, the oral drug components can be combined with any oral, non-toxic, pharmaceutically acceptable inert carder such as ethanol, glycerol, water and the like. Moreover, when desired or necessary, suitable binders, lubricants, distintergrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium sterate, magnesium sterate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carders to which the compound molecules are coupled. The compounds of the present invention may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anticoagulation agents or thrombolytic agents such as plasminogen activators or streptokinase to achieve synergystic effects in the treatment of various vascular pathologies. They may also be combined with heparin, aspirin, or warfarin.

Preferred compounds of the invention are selected from the group consisting of:

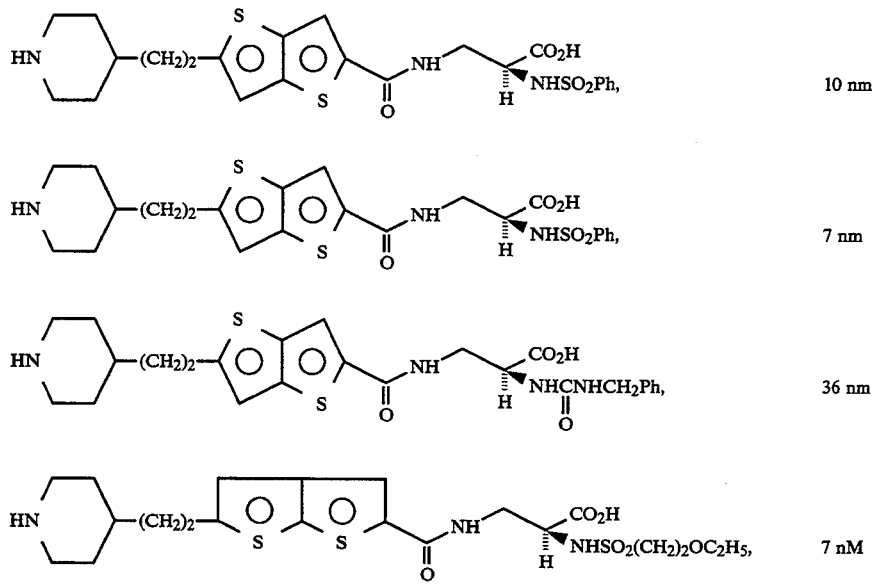

| Structure | Activity |
|---|---|
| piperidine-(CH₂)₂-furo[2,3-b]thiophene-C(O)NH-CH(CO₂H)(NHSO₂-pyridyl) | 8 nM |
| piperidine-(CH₂)₂-thieno[3,2-b]thiophene-C(O)NH-CH(CO₂H)(NHSO₂-thienyl) | 13 nM |
| piperidine-(CH₂)₂-thieno[3,2-b]furan... -C(O)NH-CH(CO₂H)(NHSO₂C₄H₉) | 32 nM |
| ... NHSO₂-pyridyl | 8 nM |
| ... NHSO₂Ph | 8 nM |
| ... β-alanine CO₂H | 410 nM |
| ... NHC(O)NHCH₂Ph | 76 nM |
| furo-thieno ... CO₂H | 350 nM |
| ... NHSO₂Ph | 8 nM |
| ... NHSO₂C₄H₉ | 5 nM |
| ... OH | 42 nM |
| ... CH₂OH, CO₂Na | 800 nM |

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the compound to be tested. The aggregation is initiated by adding 10mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus.

In addition to the following preparative procedures, several examples of in-vitro bioactivity of compounds within the scope of the present invention are indicated. To illustrate, one test which is used to evaluate fibrinogen receptor antagonist activity is based on evaluation of the inhibition of ADP-stimulated platelet aggregation. Aggregation requires that fibrinogen bind to and occupy the platelet fibrinogen receptor site. Inhibitors of fibrinogen binding inhibit platelet aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Therapeutic Treatment

Compounds of the invention may be used for inhibiting integrin protein-complex function relating to cell attachment activity. They may be administered to patients where inhibition of human or mammalian platelet aggregation or adhesion is desired.

Compounds of the invention may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

The following table exemplifies additional compounds falling within the scope of the present invention.

| X | Y | Z | A | B | E | D | L | M |
|---|---|---|---|---|---|---|---|---|
| H₂N | CH₂ | CH₂ | CH | O | CH | S | -C(=O)NH- | -CH(CH₃)CH₂CO₂H |
| CH₃NH | CH₂ | O | CH | S | CH | O | -NHC(=O)- | -CH(OH)CH₂CH₂CO₂H |
| CH₃(Ph)N | -C(=O)CH₂- | NH | CH | S | CH | S | -CN(OCH₃)- (CH₃ on N) | -CH(OCH₂Ph)CH₂CH₂CO₂H |
| piperidin-1-yl | (CH₂)₆ | N(CH₃) | CH | S | CH | S | -CH₂SCH₂- | -CH(NHSO₂CH₃)(CH₂CH₂CH₃) with CO₂CH₃ |
| morpholin-4-yl | -CH₂CH(C₂H₅)CH₂- | N(CH₂Ph) | CH | NH | CH | S | -CH₂S(O)CH₂- | -CH₂C(=O)CH₂OC(CH₃)₃ |
| azetidin-1-yl | -CH₂NC(=O)(CH₂OCH₃)CH₂- | (CH₂)₂ | CH | NH | CH | O | -CH₂SO₂CH₂- | -CH₂C(=O)NHCH(CH₂Ph)CO₂H |
| pyridin-1-yl | -CH₂NC(=O)(C₂H₅)- | (CH₂)₃ | CH | O | CH | S | -CH=CH- | -CH₂C(=O)NHCH(CH₃)CO₂H |
| oxazolidin-3-yl | (CH₂)₃O(CH₂)₂ | -C(=O)NH- | CH | O | CH | NH | -C≡C- | -CH₂CH(CH₂Ph)C(=O)COOH |

-continued

| X | Y | Z | A | B | D | E | L | M |
|---|---|---|---|---|---|---|---|---|
|  | O(CH$_2$)$_4$ | -N(CH$_3$)-C(=O)- | O | CH | CH | S | SO$_2$NH | (CH$_2$)$_2$-CH$_2$-C(=O)OH |
| 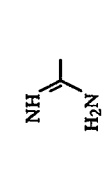 | (CH$_2$)$_5$O | -C(=O)-CH$_2$CH$_2$- | O | CH | S | S | SO$_2$N(CH$_3$) | CH$_2$-CH-CO$_2$H NHC(=O)NHCH$_3$ |
| 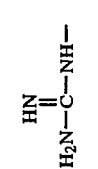 | (CH$_2$)$_2$SO$_2$(CH$_2$)$_3$ | S=CCH$_2$ | O | CH | S | CH | O=CNH | CH$_2$-CH-CO$_2$H O=CNHC$_2$H$_5$ |
| 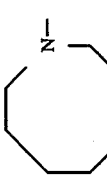 | CH$_2$SO$_2$ | NH | CH | NH | CH | N(CH$_3$) | O=C | CO$_2$CH$_2$Ph CH$_2$NHC$_2$H$_5$ |
| 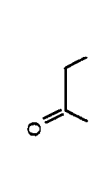 | (CH$_2$)$_2$NHSO$_2$ | N(CH$_3$) | O | CH | O | CH | SO$_2$ | CO$_2$H |
| 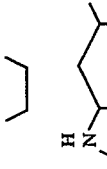 | NHSO$_2$(CH$_2$)$_2$ | (CH$_2$)$_2$ | S | CH | O | CH | O=CN(CH$_3$) | CH$_3$ CO$_2$H O=C-CH$_2$Ph |
| 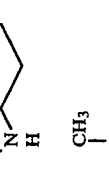 | (CH$_2$)$_3$C(=O)CH$_2$ | CH$_2$ | O | CH | S | CH | CH$_2$ | CH$_3$ CO$_2$H CH$_3$ |
|  | | | | | | | | Ph CO$_2$H OCH$_3$ |

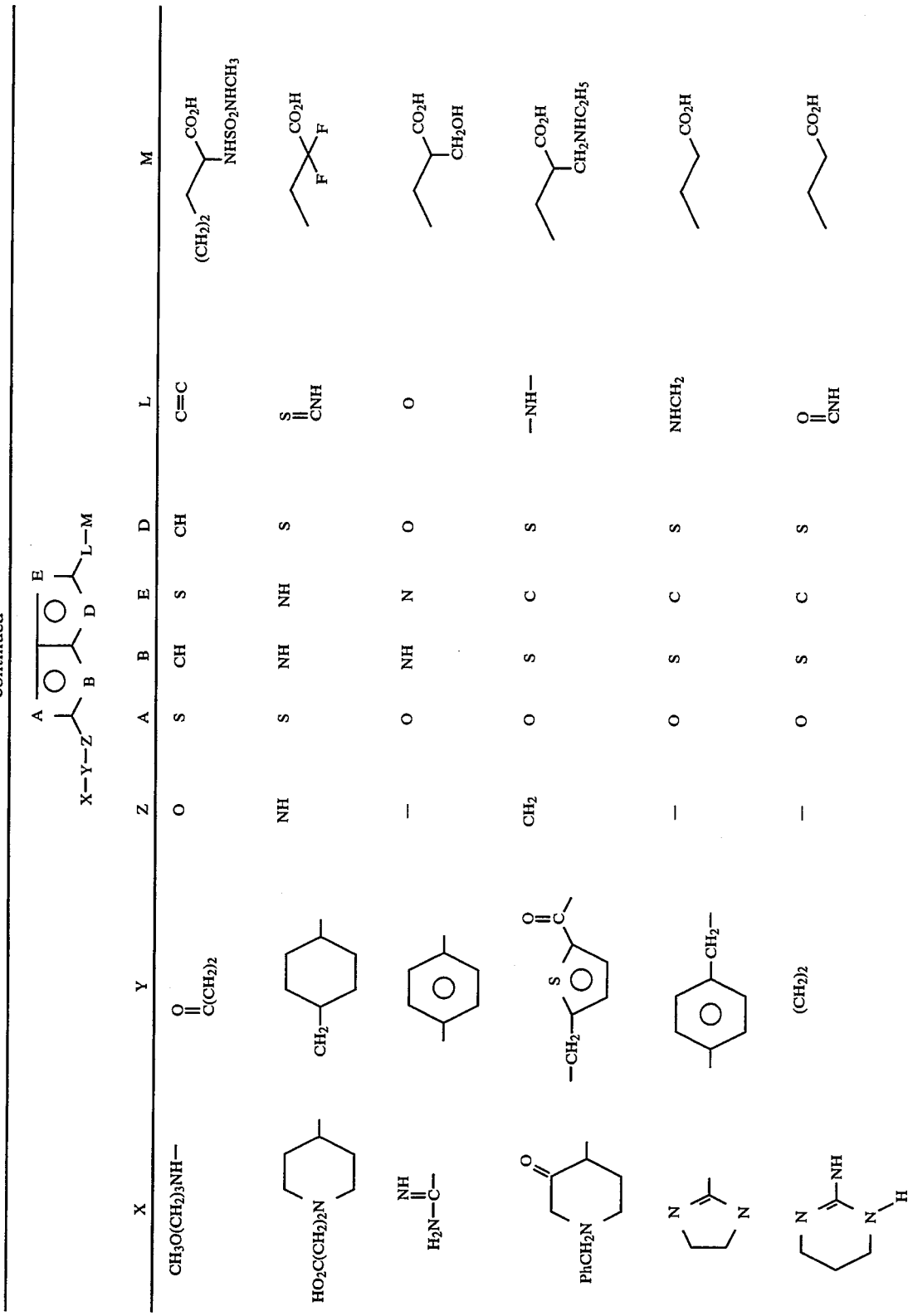

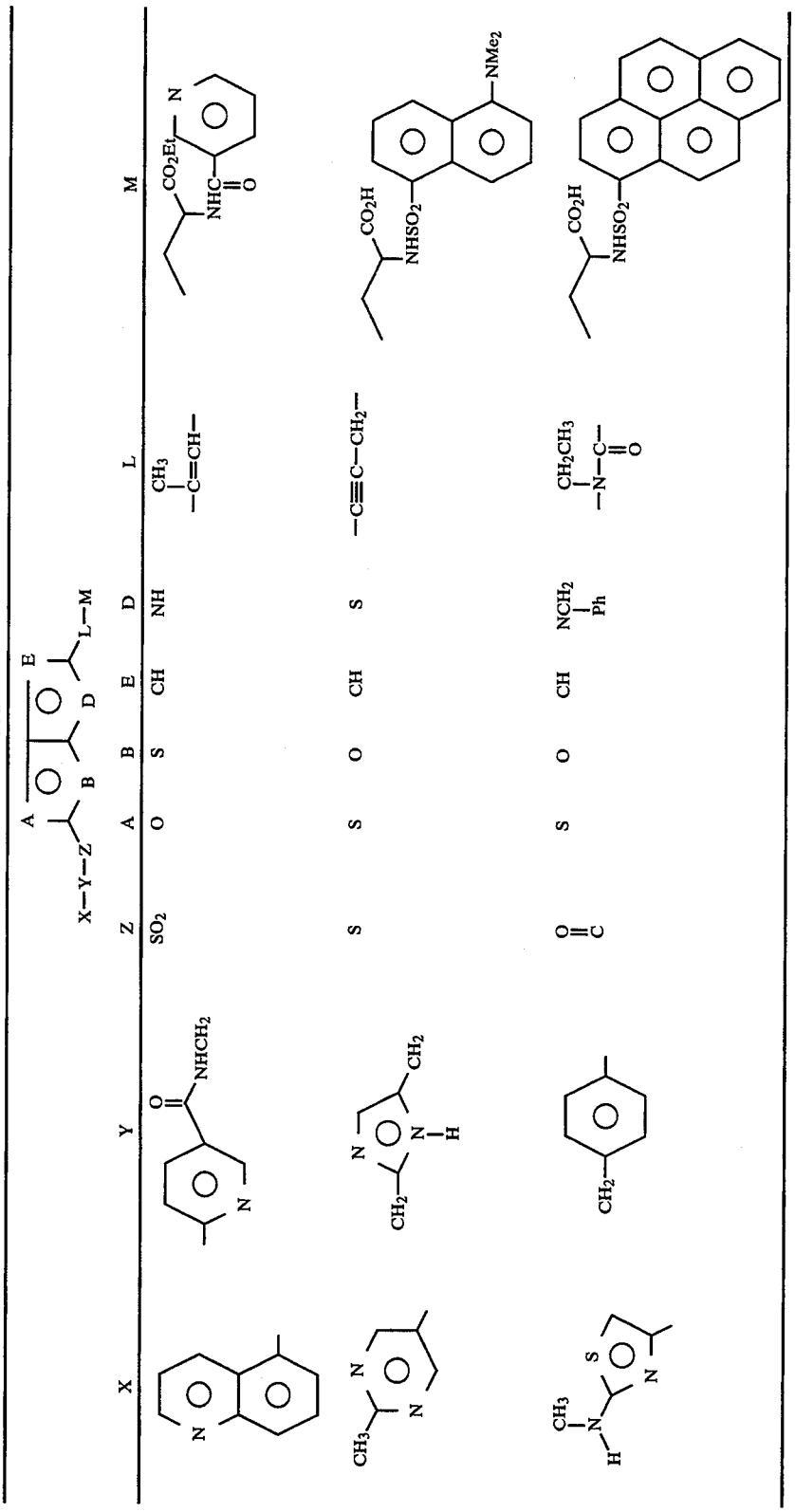

What is claimed is:

1. A compound of formula I

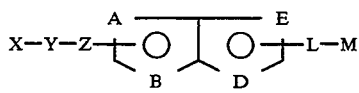  I or a pharmaceutically acceptable salt thereof wherein:
A and B are independently selected from the group consisting of C,O and S, wherein one of A or B is O or S, and
D and E are independently selected from the group consisting of C, O and S, wherein one of D or E is O or S;
X is

Y is $(CH_2)_q$, $(CH_2)_q$ ($C_{4-10}$ cycloalkyl), $(CH_2)_qNR^3—CO(CH_2)_q$, $(CH_2)_qCONR^3(CH_2)_q$, $(CH_2)_q—O—(CH_2)_q$, $(CH_2)_q—S(O_n)—(CH_2)_q$, or $(CH_2)_q—SO_2—NR^3(CH_2)_q—$, $(CH_2)_qCO(CH_2)_q$, $(CH_2)_{0-6}$ phenyl$(CH_2)_{0-6}$, $(CH_2)_{0-6}$ imidazolyl$(CH_2)_{0-6}$,

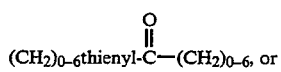

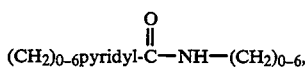

wherein q is an integer chosen from 0–8;
Z and L are independently chosen from

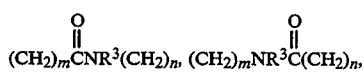

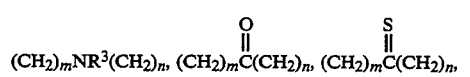

$(CH_2)_mSO_2(CH_2)_n$, $(CH_2)_mS(CH_2)_n$, $(CH_2)_mSO(CH_2)_n$, $(CH_2)_mSO_2NR^3(CH_2)_n$, $(CH_2)_mNR^3SO_2(CH_2)_n$, $(CH_2)_mCR^3=CR^4(CH_2)_n$, $(CH_2)_mC\equiv C(CH_2)_n$, $(CH_2)_m$, and $(CH_2)_mO(CH_2)_n$, where m and n are integers independently chosen from 0–6, and where $R^3$ and $R^4$ are independently selected from the group consisting of hydrogen, $C_{1-10}$ alkyl, phenyl $C_{0-8}$ alkyl, OXO, thio, amino $C_{0-8}$ alkyl, $C_{1-3}$ alkylcarbonylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $_{0-6}$ alkyloxy, or hydroxy $C_{0-6}$ alkyl, where m and n are integers independently chosen from 2–5;
M is:

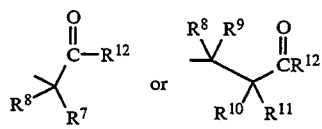

wherein $R^7$, $R^8$, $R^9$, $R^{10}$, $R^{11}$ are independently chosen from: hydrogen, fluorine, $C_{1-8}$ alkyl, hydroxyl, hydroxy $C_{1-6}$ alkyl, carboxy $C_{0-6}$ alkyl, $C_{1-6}$ alkyloxy, phenyl $C_{0-6}$ alkyloxy, $C_{1-6}$ alkylcarbonyl, phenyl $C_{0-6}$ alkylcarbonyl, $C_{1-6}$ alkylcarbonyloxy, phenyl $C_{0-6}$ alkylcarbonyloxy, $C_{1-6}$ alkylaminocarbonyloxy $C_{0-6}$ alkyl, $C_{3-8}$ cycloalkyl, phenyl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, phenyl $C_{0-6}$ alkylsulfonylamino $C_{0-6}$ alkyl, pyridyl $C_{0-6}$ alkylsulfonylamino $C_{0-6}$ alkyl, thienyl $C_{0-6}$ alkylsulfonylamino $C_{0-6}$ alkyl, naphthyl $C_{0-6}$ alkylsulfonylamino $C_{0-6}$ alkyl, pyryl $C_{0-6}$ alkylsulfonylamino $C_{0-6}$ alkyl, $C_{1-8}$ alkyloxycarbonylamino $CO_{0-8}$-alkyl, $C_{1-8}$ alkylcarbonylamino $C_{0-6}$ alkyl, pyridyl $C_{0-6}$ alkylcarbonylamino $C_{0-6}$ alkyl, $C_{0-8}$ alkylaminocarbonylamino $C_{0-6}$ alkyl, phenyl $C_{0-8}$ alkylaminocarbonylamino $C_{0-6}$ alkyl, $C_{0-8}$ alkylaminosulfonylamino $C_{0-6}$ alkyl, $C_{1-6}$ alkylsulfonyl $C_{0-6}$ alkyl, $C_{1-6}$ alkylcarbonyl $C_{0-6}$ alkyl, phenyl $C_{0-6}$ alkylcarbonyl $C_{0-6}$ alkyl, $C_{1-6}$ alkylthiocarbonylamino $C_{0-6}$ alkyl; and
$R^{12}$ is chosen from hydroxy, $C_{1-8}$ alkyloxy, phenyl $C_{0-6}$ alkyloxy, $C_{1-8}$ alkylcarbonyloxy $C_{1-4}$ alkyloxy, or a naturally occurring L- or D-amino acid joined by an amide linkage and wherein the carboxylic acid moiety of said amino acid is as the free acid or is esterified by $C_{1-6}$ alkyl.

2. A compound of claim 1 having the formula

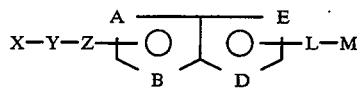

A and B are independently selected from the group consisting of C, O and S, wherein one of A or B is O or S, and
D and E are independently selected from the group consisting of C, O and S, wherein one of D or E is O or S;
X is

Y is $(CH_2)_q$, $(CH_2)_qNR^3—CO(CH_2)_q$, $(CH_2)_qCONR_3(CH_2)_q$, $(CH_2)_q—O—(CH_2)_q$, $(CH_2)_q—S(O_n)(CH_2)_1$, $(CH_2)_q—SO_2—NR^3(CH_2)_q$, $(CH_2)_{0-6}$ phenyl $(CH_2)_{0-6}$, or $(CH_2)_{0-6}$ imidazolyl $(CH_2)_{0-6}$
wherein q is an integer chosen from 0–8;
Z and L are independently chosen from:

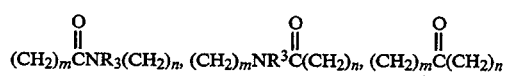

$(CH_2)_mSO_2(CH_2)_n$, $(CH_2)_mSO_2NR^3(CH)_n$, $(CH)_mNR^3SO_2(CH_2)_n$, or $(CH_2)_m$, where m and n are integers independently chosen from 0–6;

M is:

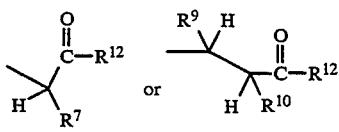

wherein $R^7$, $R^9$, and $R^{10}$ are independently chosen from: hydrogen, fluorine, hydroxyl, $C_{1-8}$ alkyl, $C_{3-8}$ cycloalkyl, phenyl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, phenyl $C_{0-6}$ alkylsulfonylamino $C_{0-6}$ alkyl, pyridyl $C_{0-6}$ alkylsulfonylamino $C_{0-6}$ alkyl, thiolyl $C_{0-6}$ alkylsulfonylamino $C_{0-6}$ alkyl, naphthyl $C_{0-6}$ alkylsulfonylamino $C_{0-6}$ alkyl, pyryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, pyridyl $_{0-6}$ alkylcarbonylamino $C_{0-6}$ alkyl, $C_{0-8}$ alkylaminosulfonylamino $C_{0-6}$ alkyl, phenyl $C_{0-8}$ alkylaminocarbonylamino $C_{0-6}$ alkyl, $C_{0-8}$ alkylaminocarbonylamino $C_{0-6}$ alkyl, $C_{1-6}$ alkylsulfonyl $C_{0-6}$ alkyl, $C_{1-6}$ alkylcarbonyl $C_{0-6}$ alkyl, and phenyl $C_{0-6}$ alkylcarbonyl $C_{0-6}$ alkyl;

$R^{12}$ is chosen from hydroxy, $C_{1-8}$ alkyloxy, phenyl $C_{0-6}$ alkyloxy, $C_{1-8}$ alkylcarbonyloxy $C_{1-4}$ alkyloxy, or a pharmaceutically acceptable salt thereof.

3. A compound of claim 2 having the formula

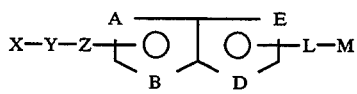

or a pharmaceutically acceptable salt thereof, wherein:
A and B are independently selected from the group consisting of C, O and S, wherein one of A or B is O or S, and
D and E are independently selected from the group consisting of C, O and S, wherein one of D or E is O or S;
X is

Y is $(CH_2)_q$, $(CH_2)_qNR^3—CO(CH_2)_q$, $(CH_2)_qCONR^3(CH_2)_q$, $(CH_2)_q—O—(CH_2)_q$, or $(CH_2)_q—S(O_n)—(CH_2)_q$, wherein q is an integer chosen from 0–8;

Z and L are independently chosen from:

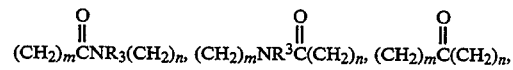

$(CH_2)_mSO_2(CH_2)_n$, and $(CH_2)_m$, where m and n are integers independently chosen from 0–6;
M is:

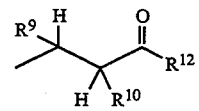

wherein $R^9$ and $R^{10}$ are independently chosen from: hydrogen, fluorine, $C_{1-8}$ alkyl, $C_{3-8}$ cycloalkyl, phenyl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, phenyl $C_{0-6}$ alkylsulfonylamino $C_{0-6}$ alkyl, pyridyl $C_{0-6}$ alkylsulfonylamino $C_{0-6}$ alkyl, thiolyl $C_{0-6}$ alkylsulfonylamino $C_{0-6}$ alkyl, naphthyl $C_{0-6}$ alkylsulfonylamino $C_{0-6}$ alkyl, pyryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, pyridyl $C_{0-6}$ alkylcarbonylamino $C_{0-6}$ alkyl, $C_{0-8}$ alkylaminocarbonylamino $C_{0-6}$ alkyl, phenyl $C_{0-8}$ alkylaminocarbonylamino $C_{0-8}$ alkyl, $C_{0-8}$ alkylaminocarbonylamino $C_{0-6}$ alkyl, $C_{1-6}$ alkylsulfonyl $C_{0-6}$ alkyl, $C_{1-6}$ alkylcarbonyl $C_{0-6}$ alkyl, or phenyl $C_{0-6}$ alkylcarbonyl $C_{0-6}$ alkyl; and
$R^{12}$ is chosen from hydroxy, $C_{1-8}$ alkyloxy, and phenyl $C_{0-6}$ alkyloxy.

4. A compound of claim 3 selected from the group consisting of:

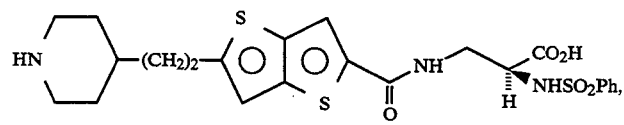

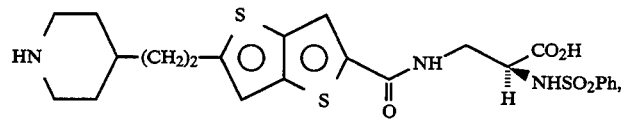

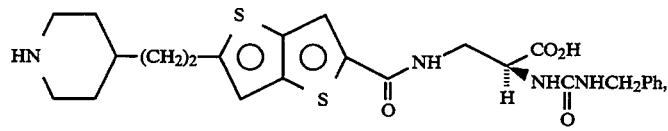

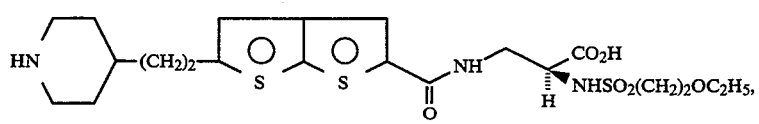
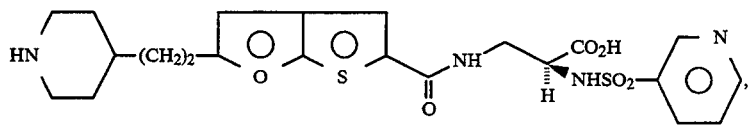
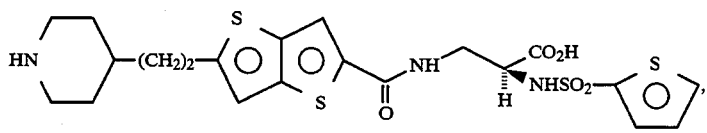
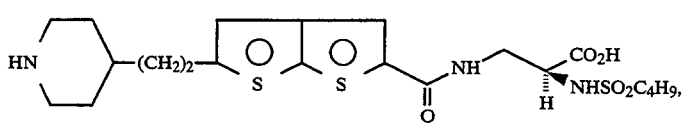
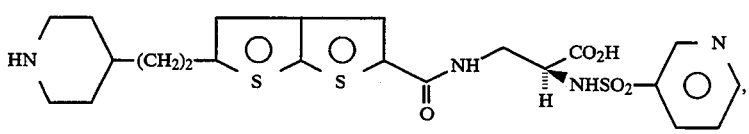
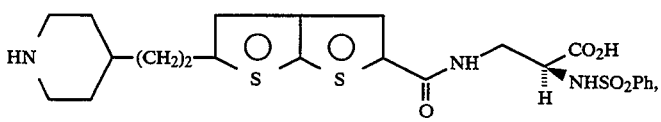
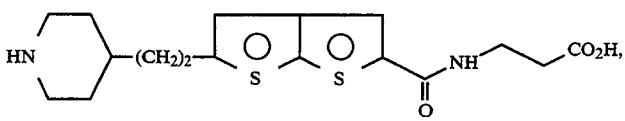
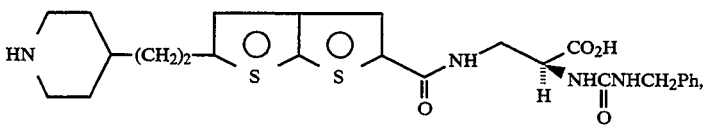
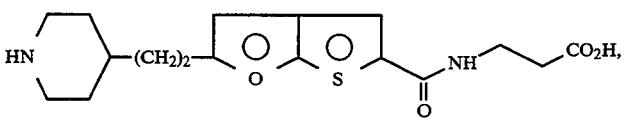
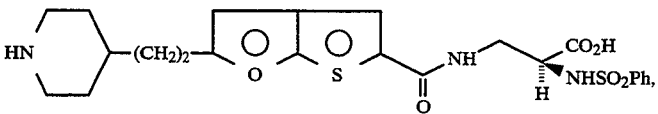
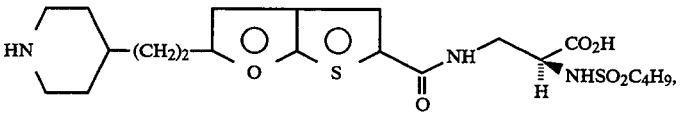
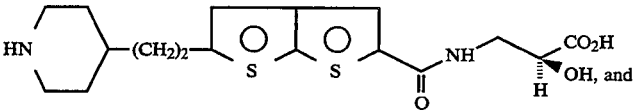

-continued

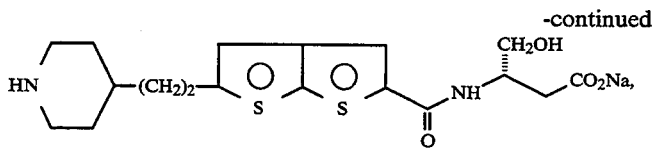

and pharmaceutically acceptable salts thereof.

5. A composition for inhibiting the aggregation of blood platelets in a mammal, comprising an antifibrinogen binding amount of a compound of claim 1 and a pharmaceutically acceptable carrier.

6. A composition for inhibiting the aggregation of blood platelets in a mammal, comprising an antifibrinogen binding amount of a compound of claim 4 and a pharmaceutically acceptable carrier.

7. A method for inhibiting the aggregation of blood platelets in a mammal, comprising administering to the mammal a composition of claim 5.

8. A method for inhibiting the aggregation of blood platelets in a mammal, comprising administering to the mammal a composition of claim 6.

* * * * *